(12) United States Patent
Zheng

(10) Patent No.: US 6,890,750 B1
(45) Date of Patent: May 10, 2005

(54) COMPOSITION AND METHODS UTILIZING STABLE REPORTER CELL LINES FOR DETECTION OF CHOP-DEPENDENT SIGNAL TRANSDUCTION

(75) Inventor: Chao-Feng Zheng, San Diego, CA (US)

(73) Assignee: Stratagene California, LaJolla, CA (US)

( * ) Notice: Subject to any disclaimer, the term of this patent is extended or adjusted under 35 U.S.C. 154(b) by 139 days.

(21) Appl. No.: 09/637,550

(22) Filed: Aug. 11, 2000

Related U.S. Application Data

(60) Provisional application No. 60/150,942, filed on Aug. 26, 1999.

(51) Int. Cl.[7] .......................... C12N 5/00; C12N 15/63; C12Q 1/68; C07H 21/02; C07H 21/04
(52) U.S. Cl. .......................... 435/325; 435/6; 435/91.1; 435/455; 536/23.1; 536/23.5; 536/24.1; 536/23.4
(58) Field of Search .......................... 435/6, 91.1, 455, 435/7.8, 7.72, 7.9, 8, 366, 367, 325; 536/23.1, 24.1, 24.5, 23.4, 23.5

(56) References Cited

U.S. PATENT DOCUMENTS 5,620,881 A * 4/1997 Wieder et al. ........... 435/172.3

OTHER PUBLICATIONS

Gopal, T.V. Molecular and Cell. Biol. 1985. vol. 5, No. 5, pp. 1199–1190.*
XiaoZhong Wang et al., SCIENCE, vol. 272, May 31, 1996, pp. 1347–1349.*
Anning Lin et al., SCIENCE, vol. 268, Apr. 14, 1995, pp. 286–290.*
Balchwal et al., *Control of c–Jun Activity by Interaction of a Cell–Specific Inhibitor with Regulatory Domain : Differences between v– and c–Jun*, 1990, Cell, vol. 63, pp. 815–825.
Bouton et al., *Transformation by pp60$^{src}$ or Stimulation of Cells with Epidermal Growth Factor Induces the Stable Association of Tyrosine–Phosphorylated Cellular Proteins with GTPase–Activating Protein*, 1991, Molecular and Cellular Biology, pp 945–953.
Braselmann et al., *A Selective Transcriptional Induction System for Mammalian Cells Based on Ga14–Estrogen Receptor Fusion Proteins*, 1993, Proc. Natl. Acad. Sci. USA, vol. 90, pp. 1657–1661.
Enslen et al., *Regulation of Mitogen–Activated Protein Kinases by a Calcium/Calmodulin–Dependent Protein Kinase Cascade*, 1996, Proc. Natl. Acad. Sci. USA, vol. 93, pp. 10803–10808.

Hill et al, *Functional Analysis of a Growth Factor–Responsive Transcription Factor Complex*, Cell, vol. 73, pp. 395–406, 1993.
Livingstone et al., *ATF–2 Contains a Phosphorylation–Dependent Transcriptional Activation Domain*, 1995, the EMBO Jounal, vol. 4 No. 8, pp. 1785–1797.
Jausons–Loffreda et al., *Chimeric Receptors as a Tool for Luminescent Measurement of Biological Activities of Steriod Hormones*, 1994, J. Biolumin Chemilumin, pp. 217–221.
Louvion et al., *Fusion of GAL4–VP16 to a Steriod–Binding Domain Provides a Tool for Gratuitous Induction of Galactose–Responsive Genes in Yeast*, 1993, Gene, vol. 131, pp. 129–134.
Marais et al., *The SRF Accessory Protein Elk–1 Contains a Growth Factor–Regulated Transcriptional Activation Domain*, 1993, Cell, vol. 73, pp. 381–393.
Minden et al., *Selective Activation of the JNK Signaling Cascade and c–Jun Transcriptional Activity by the Small GTPases Rac and Cdc42Hs*, 1995, Cell, vol. 81, pp. 1147–1157.
Price et al., *Comparative Analysis of the Ternary Complex Factors Elk–1, SAP–1a and SAP–2 (ERP/NET)*, 1995, The EMBO Journal, vol. 14, No. 11, pp. 2589–2801.
Sadowski et al., *A Vector for Expressing GAL4(1–147) Fusions in Mammalian Cells*, 1989, Nucleic Acids Research, vol. 17, No. 18, pp. 7539.
Smeal et al., *Altering the Specificity of Signal Transduction Cascades: Positive Regulation of c–Jun Transcriptional Activity by Protein Kinase A*, 1994, The EMBO Journal, vol. 13, No. 24, pp. 6006–6010.
Thliveris et al., *Genetic Identification of the DNA Binding Domain of Escherichia Coli LexA Protein*, 1992, Proc. Natl. Acad. Sci. USA, vol. 89, pp. 4500–4504.

* cited by examiner

*Primary Examiner*—Ram R. Shukla
*Assistant Examiner*—Jane Zara
(74) *Attorney, Agent, or Firm*—Palmer & Dodge LLP; Kathleen M. Williams

(57) ABSTRACT

The invention encompasses compositions and methods which utilize a cell line comprising a stably integrated recombinant nucleic acid construct comprising: a reporter gene operably linked to a recognition sequence for a sequence-specific DNA-binding protein; and a stably integrated recombinant nucleic acid construct comprising a sequence encoding a fusion protein, the fusion protein comprising a sequence-specific DNA binding domain, wherein the DNA binding domain specifically binds the recognition sequence, and a conditionally active transactivation domain of CHOP, wherein binding of the fusion protein to the recognition sequence results in transactivation of the reporter gene when the transactivation domain fused to the DNA binding domain is activated.

1 Claim, 10 Drawing Sheets

FIGURE 3

Selection of Stable Reporter Cell Lines

Reporter Construct (w/linked DBD element)

Stably transfect

Screen for clones with low background of Reporter activity and strong response to DBD – bearing activator(s)

"Stable Reporter Cell Line"

Stably transfect with fusion transactivator plasmid

Screen for clones with strong response to pathway-specific upstream activator(s)

"Pathway-Specific Stable Reporter Cell Line"

4.1.1. pFR-Luc Plasmid

*Sequence of GAL4 Binding Element in the pFR-Luc Plasmid*

| | |
|---|---|
| GT CGGACTACTGTCCTCCG AG CGGAGTACTGTCCTCCG | SEQ ID NO:9 |
| AG CGGAGTACTGTCCTCCG AG CGGAGTACTGTCCTCCG | SEQ ID NO: 10 |
| AG CGGAGTACTGTCCTCCG AG CGGAGACTCTAGAGGG | SEQ ID NO: 11 |
| TATATAATGGATCCCCGGGT AC CGAGCTCGAATTC - - | SEQ ID NO: 5 |
| --CAGCTTGGCATTCCGGTACTGTTGGTAAATG--Luciferase | SEQ ID NO: 6 |

4.1.2. Fusion Transactivator Plasmids

GAL4 (1.147)    c-Jun (1-223)
                Elk1 (307-427)
                CHOP (1-101)
                CREB (1-283)

4.1.4. pFA-CMV Plasmid

4.2 Preparation of medium and reagents

Luciferase Asay Reagent (1 x)
    40.0mM trucube (pH7.8)
    0.5 mM ATP
    10 mM MgSO$_4$
    0.5 mM EDTA
    10.0 mM DDT
    0.5 MM coenzyme A
    0.5 mM Luciferin Cell Lysis Buffer (5 x)
    40 mM tricine (pH 7.8)
    50 mM NaCl
    2 mM EDTA
    1 mM MgSO$_4$
    5 mM DTT
    1% Triton® X-100

4.1.3. Control Plasmids

SEQUENCE LISTING

<160> NUMBER OF SEQ ID NOS: 8

<210> SEQ ID NO 1
<211> LENGTH: 6
<212> TYPE: DNA
<213> ORGANISM: Artificial Sequence
<220> FEATURE:
<223> OTHER INFORMATION: contiguous residues
<221> NAME/KEY: misc_feature
<222> LOCATION: (1)..(6)
<223> OTHER INFORMATION: contiguous residues

<400> SEQUENCE: 1 ggatcc                                                                 6

```
<210> SEQ ID NO 2
<211> LENGTH: 6
<212> TYPE: DNA
<213> ORGANISM: Artificial Sequence
<220> FEATURE:
<223> OTHER INFORMATION: conserved sequence
<221> NAME/KEY: misc_feature
<222> LOCATION: (1)..(6)
<223> OTHER INFORMATION: conserved sequence
      n at position 3 is any purine residue.
      n at position 4 is any pyrimidine residue

<400> SEQUENCE: 2 ggnncc                                                                  6

<210> SEQ ID NO 3
<211> LENGTH: 99
<212> TYPE: PRT
<213> ORGANISM: Unknown
<220> FEATURE:
<223> OTHER INFORMATION: mammalian c-Jun sequence
<221> NAME/KEY: DOMAIN
<222> LOCATION: (1)..(99)
<223> OTHER INFORMATION: transactivation domain

<400> SEQUENCE: 3

Met Ala Ala Glu Ser Leu Pro Phe Thr Leu Glu Thr Val Ser Ser Trp
1               5                   10                  15

Glu Leu Glu Ala Trp Tyr Glu Asp Leu Gln Glu Val Leu Ser Ser Asp
            20                  25                  30

Glu Ile Gly Gly Thr Tyr Ile Ser Ser Pro Gly Asn Glu Glu Glu Glu
        35                  40                  45

Ser Lys Thr Phe Thr Thr Leu Asp Pro Ala Ser Leu Ala Trp Leu Thr
    50                  55                  60

Glu Glu Pro Gly Pro Thr Glu Val Thr Arg Thr Ser Gln Ser Pro Arg
65                  70                  75                  80

Ser Pro Asp Ser Ser Gln Ser Ser Met Ala Gln Glu Glu Glu Glu Glu
                85                  90                  95

Glu Gln Gly

<210> SEQ ID NO 4
<211> LENGTH: 17
<212> TYPE: DNA
<213> ORGANISM: Unknown
<220> FEATURE:
<223> OTHER INFORMATION: DNA binding domain recognition seqeunce
<221> NAME/KEY: misc_feature
<222> LOCATION: (1)..(17)
<223> OTHER INFORMATION: DNA binding domain

<400> SEQUENCE: 4
cggagtactg tcctccg                                                      17

<210> SEQ ID NO 5
<211> LENGTH: 149
<212> TYPE: DNA
<213> ORGANISM: Unknown
<220> FEATURE:
<223> OTHER INFORMATION: protein binding domain
<221> NAME/KEY: misc_feature
<222> LOCATION: (1)..(149)
<223> OTHER INFORMATION: DNA binding domain

<400> SEQUENCE: 5
gtcggagtac tgtcctccga gcggagtact gtcctccgag cggagtactg tcctccgagc      60
```

```
ggagtactgt cctccgagcg gagtactgtc ctccgagcgg agactctaga ggggtatata    120
atggatcccc gggtaccgag ctcgaattc                                      149

<210> SEQ ID NO 6
<211> LENGTH: 31
<212> TYPE: DNA
<213> ORGANISM: Artificial Sequence
<220> FEATURE:
<223> OTHER INFORMATION: Plasmid sequence
<221> NAME/KEY: misc_feature
<222> LOCATION: (1)..(31)
<223> OTHER INFORMATION: plasmid sequence

<400> SEQUENCE: 6
cagcttggca ttccggtact gttggtaaat g                                   31

<210> SEQ ID NO 7
<211> LENGTH: 74
<212> TYPE: DNA
<213> ORGANISM: Artificial Sequence
<220> FEATURE:
<223> OTHER INFORMATION: plasmid sequence
<221> NAME/KEY: misc_feature
<222> LOCATION: (1)..(74)
<223> OTHER INFORMATION: plasmid sequence

<400> SEQUENCE: 7
gtatcgccgg gatccgcccg ggctggaatt ctagaagctt ctgcagagct cggtaccaga    60
tcttgaataa gtag                                                      74

<210> SEQ ID NO 8
<211> LENGTH: 21
<212> TYPE: PRT
<213> ORGANISM: Unknown
<220> FEATURE:
<223> OTHER INFORMATION: domain
<221> NAME/KEY: DOMAIN
<222> LOCATION: (1)..(21)
<223> OTHER INFORMATION: selected fusion activation domain

<400> SEQUENCE: 8

Val Ser Pro Gly Ser Gly Arg Ala Gly Ile Leu Glu Ala Ser Ala Glu
1               5                   10                  15

Leu Gly Thr Arg Ser
            20
```

COMPOSITION AND METHODS UTILIZING STABLE REPORTER CELL LINES FOR DETECTION OF CHOP-DEPENDENT SIGNAL TRANSDUCTION

PRIORITY

This application claims priority under 35 U.S.C. §119(e) to U.S. Provisional Application No. 60/150,942, filed Aug. 26, 1999.

FIELD OF THE INVENTION

The invention relates in general to the measurement of the activation status of signal transduction pathways and/or components of these pathways in cells. More specifically, the invention relates to engineered cell lines and methods using such cell lines for the measurement of the activation/inhibition of signal transduction pathways converging at transcriptional activators in cells.

BACKGROUND OF THE INVENTION

A multicellular organism is composed of many types of cells performing specialized functions. Cells communicate with each other for the organism to function as a whole. They do so at many levels and by various mechanisms. Cell identity is determined by the proteins that are synthesized within the cell. Therefore, regulation of gene expression, especially transcription, is the key mechanism of controlling cell growth and differentiation. To control transcription in response to extracellular stimuli originating from other cells or the surrounding environment, signals from outside the cell are transmitted to the transcription machinery inside the nucleus via a variety of signaling molecules including receptors, protein kinases and phosphatases and adapters, which form networks known as signal transduction pathways, or STPs (Boulikas, 1995, *Crit. Rev. Euk. Gene Exp.* 5: 1–77; Hunter et al., 1992, *Cell* 70: 357–387; Karin and Hunter, 1995, *Curr. Biol.* 5, 747–757; Treisman, 1996, Current Opinion in *Cell Biol.* 8: 205–215). These signaling molecules are also of interest to medical science and to the pharmaceutical industry because malfunctions of these molecular pathways are the cause of many human diseases, including cancers, genetic disorders and immune diseases. Therefore, many of the intracellular signaling molecules are targets for drug intervention and targets for drug screening.

Among the best characterized STPs are the cAMP-dependent protein kinase (PKA) pathway and the mitogen-activated protein kinase (MAPK) pathways mediating signals from growth factors (e.g. EGF and NGF) and cellular stress such as heat, UV, oxidative stresses and protein synthesis inhibitors (FIG. 1). These signaling pathways receive diverse upstream signals and cause distinct downstream changes. One common feature of these pathways is that they all rely on the nuclear translocation of an activated protein kinase (e.g. MAPK or PKA) to transmit signals from outside the cell to the transcription machinery in the cell nucleus (FIG. 1). When activated by upstream signals, signal transduction kinases specific to a given pathway (e.g., MAPK or PKA) translocate into the nucleus and phosphorylate critical residues thereby activating the transactivating activity of a specific transcription factor(s), and thus converting an extracellular signal into a specific transcriptional response in the nucleus (FIG. 1). The activation status of the transcription factors therefore reflects the activation status of the respective kinases and upstream signaling molecules along the pathway.

Since the discovery of the first member of the MAPK family (Ray and Sturgill, 1987, *Proc. Natl. Acad. USA* 84: 1502–1506), more than one hundred MAPK family members have been cloned (Kultz, 1998, *J. Mol. Evol.* 46: 571–588). These signaling pathways all use a three-component protein kinase cascade consisting of MAPK/MAPK kinase/MAPK kinase kinase but receive diverse upstream signals and cause distinct downstream changes. In the budding yeast *S. cerevisiae*, at least five distinct MAP kinase pathways have been identified to function in mating (Fus3/Kss1), cell wall biosynthesis (Mpk1), osmosensing (Hog1), sporulation (SmK1) and pseudohyphal development and invasive growth pathway (Levin and Errede, 1995, *Current Opin. Cell Biol.* 7: 197–202; Waskiewicz and Cooper, 1995, *Curr. Opin. Cell. Biol.* 7, 798–805). In mammalian cells, over 12 MAPKs have been cloned and characterized (Kultz, 1998, supra; Waskiewicz, 1995, supra). Among the transcription factors activated by MAPK pathways is CHOP/GADD153, which will be referred to herein as CHOP (Wang and Ron, 1996, Science 272: 1347–1349). CHOP is activated by p38 MAPK, which is in turn activated by the MAPKK MEK3. CHOP activity thus reflects the avtivationof those factors upstream of CHOP in the activation pathway.

Transcriptional activator proteins have been found to be modular in nature, very often comprised of linked domains that retain their respective functions when separated from the remainder of the protein. This modular nature of transcription factors was originally demonstrated in the yeast GAL4 transactivator, and has subsequently been found in a wide variety of transcription factors wherein the activation domain (AD) and DNA binding domain (DBD) may be structurally and functionally separated (Ma and Ptashne, 1987, Cell 48: 847–853). An important consequence of the modular nature of transcription factors is that the isolated functional domains may confer the specific DNA binding or transactivating activity of a given transcription factor upon an unrelated fusion partner.

Fusion transactivators consisting of the DNA-binding domain of yeast GAL4 protein (amino acid residues 1–92 or 1–147; Sadowski and Ptashne, 1989, *Nucl. Acids Res.* 17: 7539) or *E. coli* LexA (residues 1–87; Thliveris and Mount, 1992, *Proc. Natl. Acad. Sci. USA* 89: 4500–4504) and the activation domains of transcription activators from higher eukaryotes have been used in the literature as sensors for specific pathways in transient transfection assays (FIG. 2; Xu et al., 1997, *Strategies* 10: 1–3; Xu et al., 1997, *Strategies* 10: 79–80; Xu et al., 1997, *Strategies* 10: 81–83; Sanchez et al., 1998, *Strategies* 11: 52–53; Baichwal and Tjian, 1990, *Cell*, 63: 815–826; Enslen et al., 1996, *Proc. Natl. Acad. Sci. USA.* 93: 10803–10808; Hill et al., 1993, *Cell*, 73: 395–406; Lin et al, 1995, *Science*, 268: 286–289; Livingstone et al, 1995, *EMBO J.*, 14: 1785–1797; Marais et al., 1993, *Cell* 73: 381–393; Minden, et al., 1995, *Cell*, 81: 1147–1157; Price et al., 1995, *EMBO J*, 14: 2589–2601; Smeal et al., 1994, *EMBO J.*, 13: 6006–6010; Wang and Ron, 1996, *Science*, 272: 1347–1349). A trans-reporting system of this kind includes a fusion transactivator plasmid that expresses a fusion protein consisting of the activation domain of a pathway-specific transcription factor and the DNA binding domain of a sequence-specific DNA binding factor. The transactivation moiety of the fusion transactivator is phosphorylated and activated by kinases specific to that activation pathway. The activity of the fusion activators, therefore, reflects the in vivo activation of the specific kinases and the corresponding signal transduction pathways. The DNA-binding domain moiety enables the fusion activator to bind one or more copies of the binding element (e.g., that from GAL4, LexA or other sequence-specific DNA binding protein) situated upstream of the reporter gene in a separate reporter vector (FIG. 2). Expression (or activity) levels of reporter gene product reflect the activation status of the signaling pathway. Therefore, the effects of a gene product or an extracellular stimulus such as a growth factor or UV irradiation can be monitored by simple and sensitive reporter assays.

The systems described above are transient transfection assay systems. Introduction of plasmid DNA into mammalian cells by transfection is still largely a trial and error process. Transfection efficiency fluctuates from cell to cell and from experiment to experiment, which can give rise to inconsistent assay results. Some applications of pathway-specific signal transduction systems, especially those involving a high volume of samples such as drug screening applications, demand more convenient format and more consistent results. There is a need in the art for pathway-specific signal transduction assay systems that provide consistent assay results.

GAL4 fusion proteins have been used to test protein:protein interactions, to study chromatin structure and function and to serve as inducible transcription factors for protein expression and the measurement of the biological activities of steroid hormones (Jausons-Loffreda et al., 1994, *J. Biolumin. Chemilumin.* 9: 217–221; Braselmann et al., 1993, *Proc. Natl. Acad. Sci. USA* 90: 1657–1661; Louvion et al., 1993, *Gene* 131: 129–134; Dang et al., 1991, *Mol. Cell. Biol.* 11, 945–962). The steroid hormone studies investigated the single component steroid hormone receptor pathway, in which the receptor itself translocates to the nucleus and transactivates gene expression after binding the hormone. Fusion proteins of this kind have not been used, however, to establish stable reporter systems responsive to multicomponent signal transduction cascade pathways such as the MAPK pathway. There is a need in the art for systems that re-create the natural cellular environment for activation involving multicomponent signal transduction cascades.

There is also a need in the art for pathway-specific signal transduction assay systems that do not require transfection, whether transient or otherwise.

SUMMARY OF THE INVENTION

The invention encompasses a cell line comprising a stably integrated recombinant nucleic acid construct comprising a reporter gene operably linked to a recognition sequence for a sequence-specific DNA-binding protein and a stably integrated recombinant nucleic acid construct comprising a sequence encoding a fusion protein, the fusion protein comprising a sequence-specific DNA binding domain, wherein the DNA binding domain specifically binds the recognition sequence, and a conditionally active transactivation domain of CHOP, wherein binding of the fusion protein to the recognition sequence results in transactivation of the reporter gene when the transactivation domain fused to the DNA binding domain is activated.

In one embodiment of the invention, the reporter gene is selected from the group consisting of genes encoding luciferase, -galactosidase, chloramphenicol acetyltransferase, secreted alkaline phosphatase, green fluorescent protein or other easily assayable reporter activity.

In another embodiment of the invention, the recognition sequence for a sequence-specific DNA-binding domain is that sequence recognized by one of the group consisting of GALA and LexA.

In another embodiment of the invention, the fusion protein is constitutively expressed.

In another embodiment of the invention, the fusion protein is constitutively expressed in a specific cell type.

In another embodiment of the invention, the cell line is of mammalian origin.

In a preferred embodiment of the invention, the parent cell line is human.

In a further preferred embodiment of the invention, the parent cell line is HeLa.

The invention also encompasses a method of assaying for the activity of CHOP signal transduction in a mammalian cell, the method comprising the steps of: detecting in a pathway-specific reporter cell line expression of a reporter gene, wherein the reporter cell line comprises: a reporter gene operably linked to a recognition sequence for a sequence-specific DNA-binding protein; and a stably integrated recombinant nucleic acid construct comprising a sequence encoding a fusion protein, the fusion protein comprising a sequence-specific DNA binding domain, wherein the DNA binding domain specifically binds the recognition sequence, and a conditionally active transactivation domain of CHOP, wherein binding of the fusion protein to the recognition sequence results in transactivation of the reporter gene when the transactivation domain fused to the DNA binding domain is activated, wherein expression of the reporter gene is indicative of the activity of the signal transduction pathway.

The invention also encompasses a method of screening for a modulator of the activation of CHOP signal transduction in a mammalian cell, the method comprising the steps of: 1) contacting a stable reporter cell line with a candidate modulator under conditions sufficient to permit activation of the signal transduction pathway, the reporter cell line comprising: a reporter gene operably linked to a recognition sequence for a sequence-specific DNA-binding protein; and a stably integrated recombinant nucleic acid construct comprising a sequence encoding a fusion protein, the fusion protein comprising a sequence-specific DNA binding domain, wherein the DNA binding domain specifically binds the recognition sequence, and a conditionally active transactivation domain of CHOP, wherein binding of the fusion protein to the recognition sequence results in transactivation of the reporter gene when the transactivation domain fused to the DNA binding domain is activated; and 2) detecting the expression of the reporter gene, wherein a difference in expression of the reporter gene in the presence of the candidate modulator and in the absence of the candidate modulator is indicative of modulatory activity of the candidate modulator on the pathway.

In one embodiment, the method further comprises, during the contacting step, providing a signal activating the conditionally active transactivation domain.

In a preferred embodiment, the providing comprises adding an activator compound to the culture medium of the reporter cell line.

In a preferred embodiment of the method, the DNA binding domain is selected from the group consisting of the DNA binding domains of GAL4 and LexA.

In a preferred embodiment of the method, the mammalian cell is human.

In a further preferred embodiment of the method, the mammalian cell is a HeLa cell.

The invention also encompasses a method of assaying for the activation of a conditionally active transactivation domain on CHOP signal transduction in a mammalian cell, the method comprising the step of: detecting in a stable reporter cell line that is subjected to conditions which permit activation of the conditionally active transactivation domain the expression of a reporter gene, the reporter cell line comprising: a reporter gene operably linked to a recognition sequence for a sequence-specific DNA-binding protein; and a stably integrated recombinant nucleic acid construct comprising a sequence encoding a fusion protein, the fusion protein comprising a sequence-specific DNA binding domain, wherein the DNA binding domain specifically binds the recognition sequence, and a conditionally active transactivation domain of CHOP, wherein binding of the fusion protein to the recognition sequence results in transactivation of the reporter gene when the transactivation domain fused to the DNA binding domain is activated; wherein detection of expression of the reporter gene is indicative of the activity of the conditionally active transactivating protein.

The invention also encompasses a method of screening for a modulator of the activity of a conditionally active transactivation domain on CHOP signal transduction in a mammalian cell, the method comprising the steps of: 1) contacting a stable reporter cell line with a candidate modulator under conditions sufficient to permit activation of CHOP signal transduction, the reporter cell line comprising: a reporter gene operably linked to a recognition sequence for a sequence-specific DNA-binding protein; and a stably integrated recombinant nucleic acid construct comprising a sequence encoding a fusion protein, the fusion protein comprising a sequence-specific DNA binding domain, wherein the DNA binding domain specifically binds the recognition sequence, and a conditionally active transactivation domain of CHOP, wherein binding of the fusion protein to the recognition sequence results in transactivation of the reporter gene when the transactivation domain fused to the DNA binding domain is activated; and 2) detecting the expression of the reporter gene, wherein a difference in expression of the reporter gene in the presence of the candidate modulator and in the absence of the candidate modulator is indicative of modulation of the activity of the conditionally active transactivating protein.

In one embodiment, the method further comprises, during the contacting step, providing a signal activating the conditionally active transactivation domain.

In a preferred embodiment of the method, providing comprises adding an activator compound to the culture medium of the reporter cell line.

In another embodiment of the method, the DNA binding domain is selected from the group consisting of the DNA binding domains of GAL4 and LexA.

In another embodiment of the method, the mammalian cell is human.

In a preferred embodiment of the method, the mammalian cell is a HeLa cell.

The invention also encompasses a kit comprising a cell line of the invention, and packaging therefor.

The invention also encompasses a kit for performing a method using a cell line of the invention as disclosed herein and packaging for the kit.

In a preferred embodiment, the invention encompasses a kit for performing a method as disclosed herein, further comprising a nucleic acid expression construct encoding an upstream activator of the conditionally active transactivation domain.

As used herein, the term "parent cell line" refers to a cell line that is transfected to generate a reporter cell line or a pathway-specific reporter cell line according to the invention. A parent cell line must be eukaryotic, and is preferably a mammalian cell line, and more preferably a human cell line, and does not contain a recombinant DNA containing the activation doamin fused to the reporter gene.

As used herein, a "reporter cell line" is a cell line that carries a stably integrated reporter gene operably linked to a recognition sequence for the DNA binding domain of a sequence-specific DNA binding protein.

As used herein, the term "pathway-specific reporter cell line" refers to a reporter cell line in which the activity of the reporter gene reflects the activity of signal transduction pathways converging on a particular conditionally active transactivating protein or protein domain. A pathway-specific reporter cell line carries, in addition ot a reporter construct, a conditionally active fusion transactivator protein construct that activates expression of the reporter in response to activation of a particular signal transduction pathway.

As used herein, the term "stably integrated" refers to incorporation of a nucleic acid construct into the genome of a host cell such that it is replicated when the genome is replicated and is passed onto the progeny cells upon cell division for at least two cell divisions and preferably for at least ten, more preferably for at least twenty to thirty cell divisions. As referred to herein, a stably integrated nucleic acid construct encompasses the integration of a single copy or of two, three, or up to five, ten, twenty or even one hundred or more copies of the nucleic acid construct. Stable integration over a number of cell divisions may be assessed by determining the presence of one or more copies of the construct in a given cell preparation using, for example, PCR amplification of a region of the genome containing the construct.

As used herein, the term "reporter gene" refers to a gene sequence encoding a product that is detectable when expressed by a host cell, the expression of which product is under the control of heterologous regulatory sequences conferring responsiveness of the reporter gene to the activation of a particular regulatory pathway. In order to be useful as a reporter gene, the product, which may be an RNA transcript or a protein or protein activity, including but not limited to an enzyme or enzyme activity, should not be endogenous to the host cell, or at least should not be detectable in the host cell in an amount that renders detection of the exogenous gene product over the endogenous product impossible. Non-limiting examples of reporter genes useful in the invention include luciferase (from firefly or other species), chloramphenicol acetyltransferase, -galactosidase and green fluorescent protein. In order to be useful according to the invention, the background expression of a reporter gene (i.e., the detectable expression of the reporter in the absence of a signal that activates the regulatory pathway to which the reporter is responsive) must be low. Reporter gene background may be said to be low if an induction of 10-fold, preferably 20 fold, 30 fold, or up to 50 to 100 fold or more is detectable within the linear range of the detection assay.

As used herein, the term "sequence-specific DNA binding protein" refers to a protein that recognizes and binds a specific DNA sequence. The sequence bound by a sequence-specific DNA binding protein may be an invariant arrangement of contiguous nucleotide residues (e.g., GGATCC, SEQ ID No. 1) or it may be a conserved sequence motif in which individual residues may vary and still allow recognition and binding by the sequence-specific DNA binding protein (e.g., GGPuPyCC, SEQ ID No. 2 wherein Pu and Py are purine and pyrimidine, respectively). Binding of the protein to its specific sequence may be assessed via any conventional protein:nucleic acid binding methods, including but not limited to electrophoretic gel analysis of a given protein:nucleic acid construct.

As used herein, the term "recognition sequence" or "recognition sequence for a sequence-specific DNA binding protein" refers to the particular sequence or sequence motif of nucleic acid residues recognized and bound by a sequence-specific DNA binding protein.

As used herein, the term "DNA binding domain" refers to a portion of a sequence-specific DNA binding protein that binds to the recognition sequence on DNA. The term "DNA binding domain" is meant to encompass a whole sequence-specific DNA-binding protein as well as the particular portion or domain thereof that is sufficient to permit or mediate DNA binding. It should be understood that a DNA binding domain according to the invention has the ability when separated from the context of the whole sequence-specific DNA binding protein to bind DNA in a sequence-specific manner, and further, that it can confer this DNA binding specificity upon another protein or portion of a protein when fused to it. It should be further understood that a DNA binding domain according to the invention does not transactivate gene expression.

As used herein, the term "fusion protein" refers to a recombinant protein comprising two or more proteins, or domains or portions of two or more proteins, linked together in a manner not occurring in nature.

As used herein, the terms "transcriptional activator protein", "transactivating protein", or "transactivation domain" refer to a protein or domain of a protein which can contribute to an increase in the transcription of a gene through interactions with the enzymes and factors that assemble at the promoter of a gene to form a functional transcription complex. A transactivating protein or transactivation domain may exist in an active form, capable of effecting an increase in transcription, or in an inactive form requiring activation before effecting an increase in transcription; a transactivating protein or transactivation domain of this type is referred to herein as "conditionally active". It should be understood that a transactivating protein or transactivation domain can confer transactivating properties upon another protein or protein domain when expressed as a fusion with, or when bound to, that protein or protein domain. As used in the invention, a transactivation domain does not have sequence-specific DNA binding ability.

As used herein, the term "conditionally active" refers to a protein or domain of a protein which may exist in an active functional form or in an inactive form. This conditional activity may be regulated, for example, by phosphorylation, conformational change, or by complex formation with another protein. It should be understood that a conditionally active functional domain can confer conditional functional properties upon another protein or protein domain when expressed as a fusion with that protein or protein domain.

As used herein, the term "activator signal" refers to a treatment or an entity that activates a signal transduction pathway or portion of a pathway in a cell. Treatment with an activator signal is sufficient to activate a conditionally active transactivation domain according to the invention. An activator signal according to the invention encompasses expression of a protein that influences a signal transduction pathway. As used herein, "conditions which permit activation of a conditionally active transactivation domain" refers to those conditions which include but are not limited to subjecting the cells to an activator signal such as a chemical agent that activates a given pathway or pathways, and any physical treatment such as thermal variation, UV or X-irradiation, or induction of hypoxia or oxidative stress, such treatment resulting in the activation of a signal transduction pathway or portion of a pathway in a cell.

As used herein, the term "activator compound" refers to a compound or chemical agent that can serve to generate an activator signal.

As used herein, the term "upstream activator" refers to a protein or treatment that activates a signal transduction pathway at or before the pathway step involving a conditionally active transactivation domain being used to drive expression of a reporter gene in a pathway-specific reporter cell line of the invention.

The present invention is useful for obtaining consistent assay results in assays involving CHOP signal transduction, and employs cell lines to analyze regulation of CHOP signal transduction pathways. The invention also is useful for assessing the function of gene products in CHOP signal transduction, screening for candidate modulators of CHOP signal transduction, and analyzing protein:protein interactions in mammalian cells.

Further features and advantages of the invention will become more fully apparent in the following description of the embodiments and drawings thereof, and from the claims.

As shown in the figure by solid arrows, MAPKs are phosphorylated and activated by MAPKKs directly, and they can then directly phosphorylate and activate downstream transcriptional activators such as CHOP. There may be many steps from the cell surface or other part of the cell to the activation of MAPKKS or other downstream activators.

Figure 1:
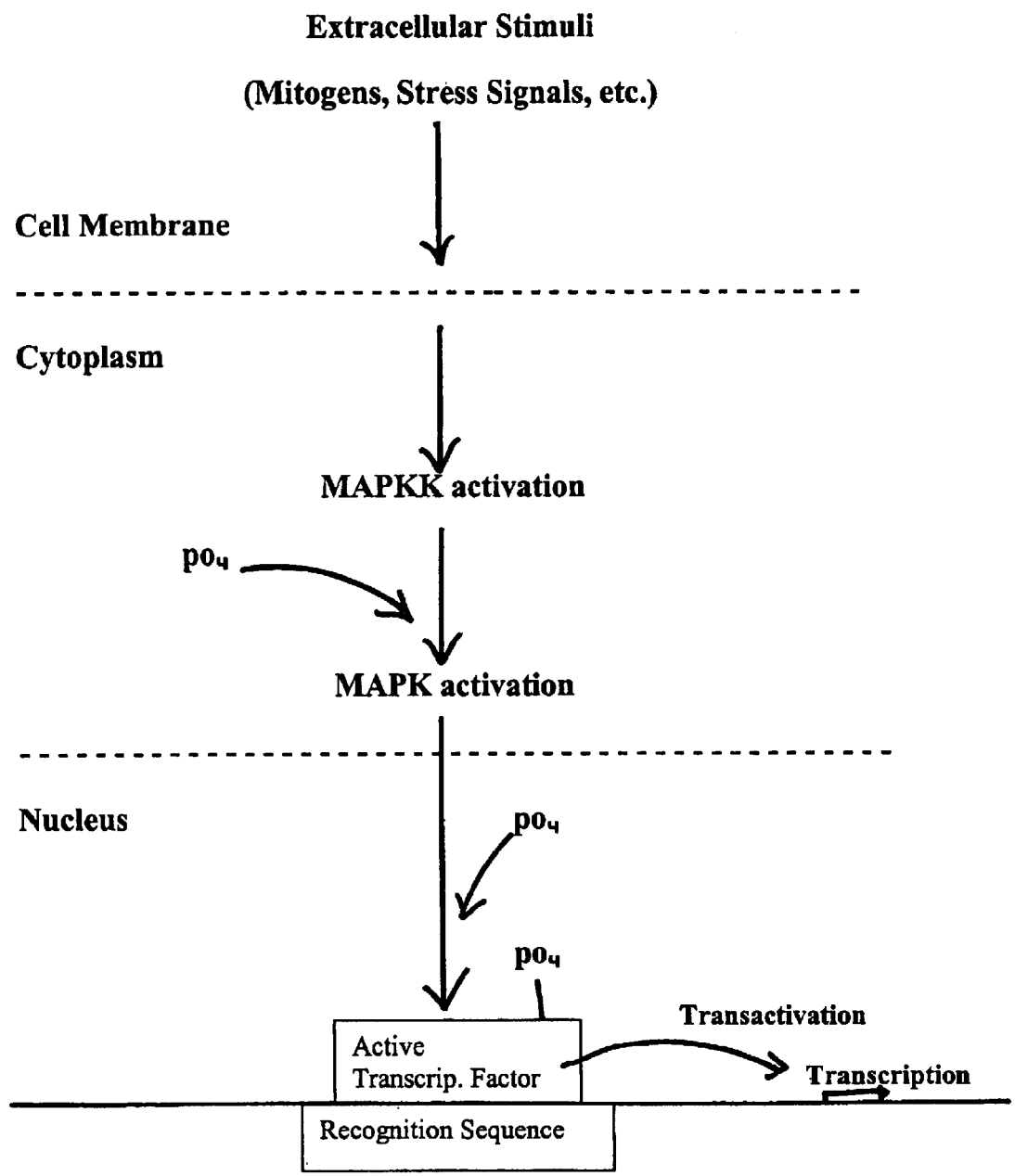
FIG. 1. Schematic of signal transduction pathways in mammalian cells.
Figure 2:
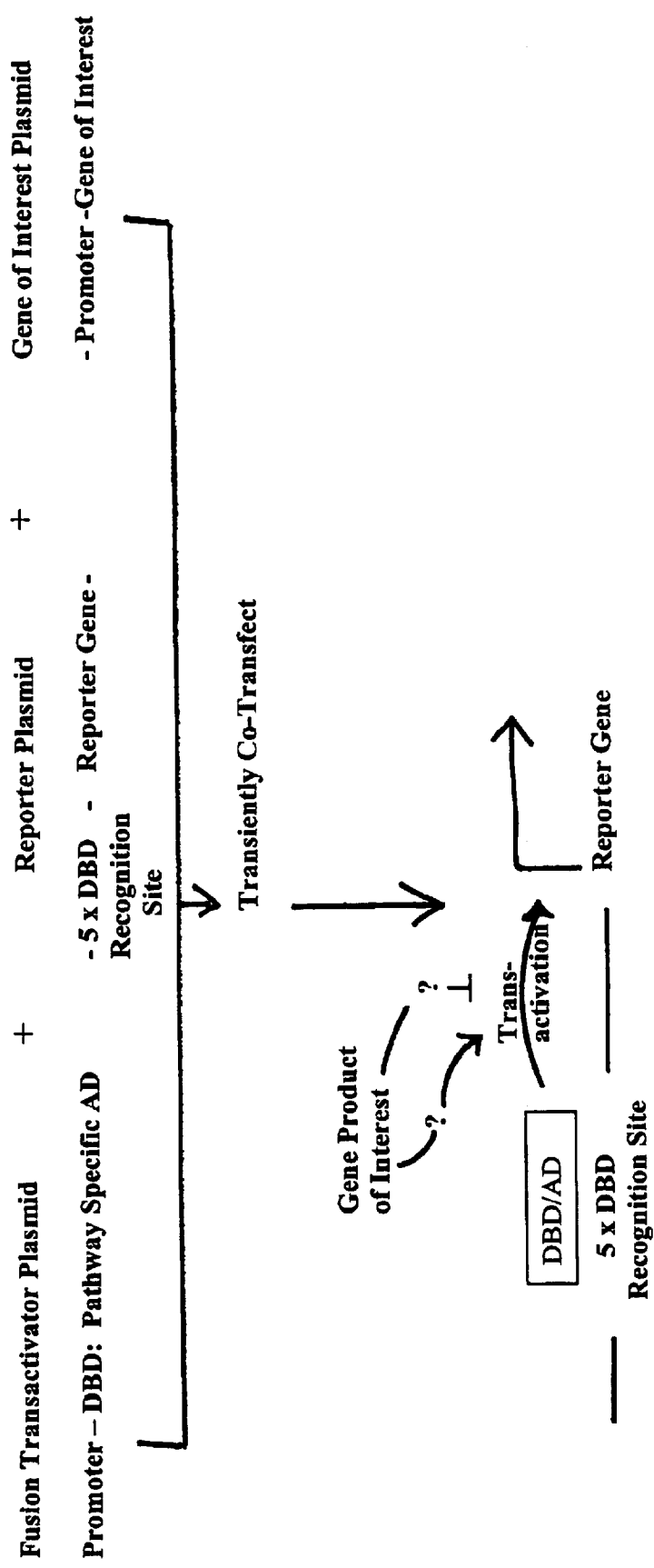

FIG. 2. Monitoring Pathway-Specific Signal Transduction.

A schematic of a pathway-specific signal transduction monitoring system is shown. A pathway-specific fusion transactivator plasmid and a reporter plasmid are cotransfected, optionally along with a plasmid encoding a gene of interest, into a eukaryotic cell. The fusion transactivator may then bind a recognition element linked to the reporter, and, depending on the activation status of the fused transactivation domain, may activate transcription of the reporter. The (positive or negative) effect of a gene of interest on the functions of the specific pathway may be determined by changes or differences in the expression of the reporter.

FIG. 3. Selection procedure for selection of stable reporter cell lines.

A schematic of the selection of stable reporter cell lines is shown. A reporter construct with a linked DNA-binding domain element(s) is stably transfected into a chosen cell line, followed by screening for clones with low background reporter activity and a strong response to activators that bind the DNA-binding domain recognition element. The singly transfected stable reporter cell line is then stably transfected with a pathway-specific fusion transactivator plasmid, followed by screening for clones with a strong response to pathway-specific upstream activator(s) to identify pathway specific stable reporter cell lines.

Figure 4:
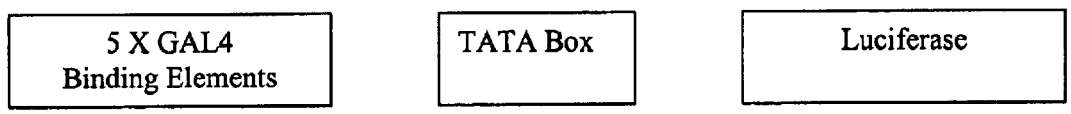

FIG. 4. Schematic of pFR-Luc reporter plasmid.

A schematic diagram of the pFR-Luc reporter vector is shown. Five copies of the GAL4 DNA-binding domain recognition sequence (underlined) are linked to a minimal promoter containing a TATA element upstream of the initiator ATG initiator codon of firefly luciferase coding sequences.

Figure 5:
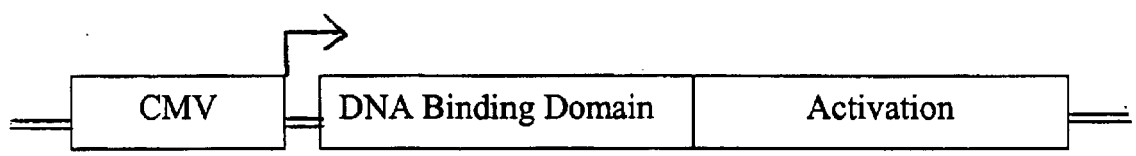

FIG. 5. Fusion transactivator plasmid.

A schematic diagram of the fusion transactivator plasmid pFA2-CHOP is shown. Expression of the GAL4 DNA binding domain (1–147):CHOP transactivation domain (1–101) fusion protein is driven by the CMV promoter.

Figure 6:
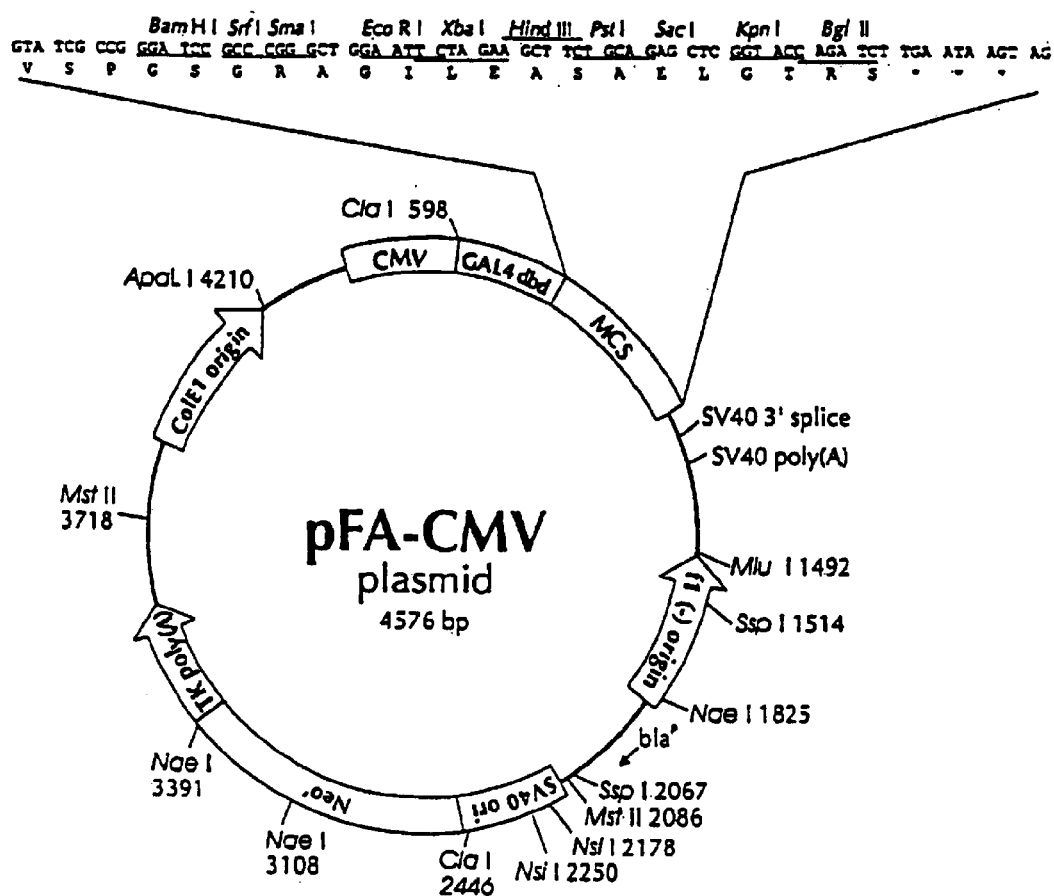

FIG. 6. pFA-CMV plasmid.

A schematic diagram of the plasmid pFA-CMV, used as the base vector for the fusion transactivator plasmid pFA2-CHOP is shown. The vector fuses the GAL4 DNA-binding domain (amino acids 1–147) to the selected fusion transactivation domain via the shown multiple cloning site. Expression of the resulting fusion transactivator protein is driven by the strong CMV promoter.

Figure 7:
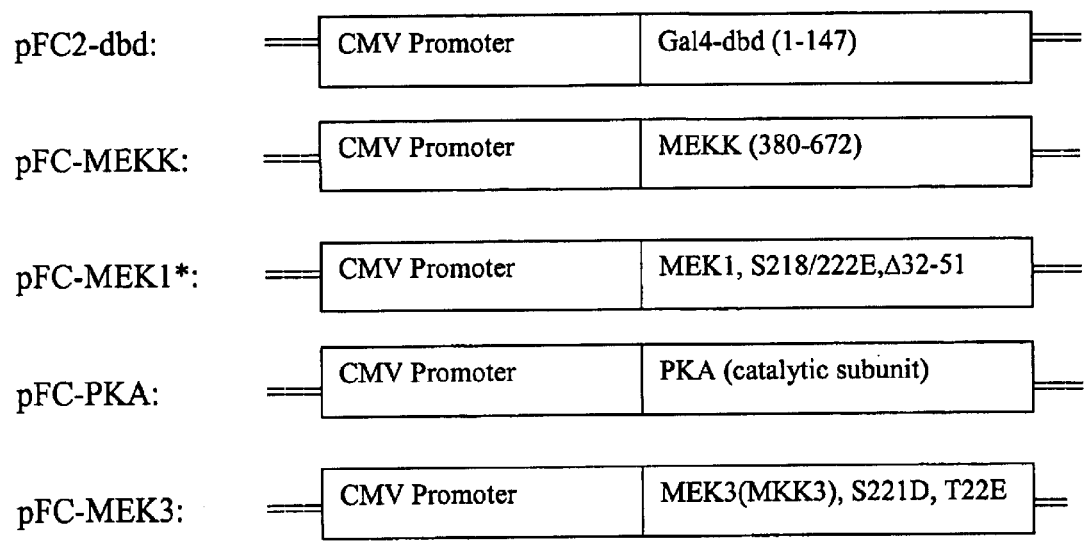

FIG. 7. Control plasmids.

Schematic diagrams of the control plasmids pFC2-DBD (encoding GAL4 DNA-binding domain alone) and pFC-MEK3.

Figure 8:
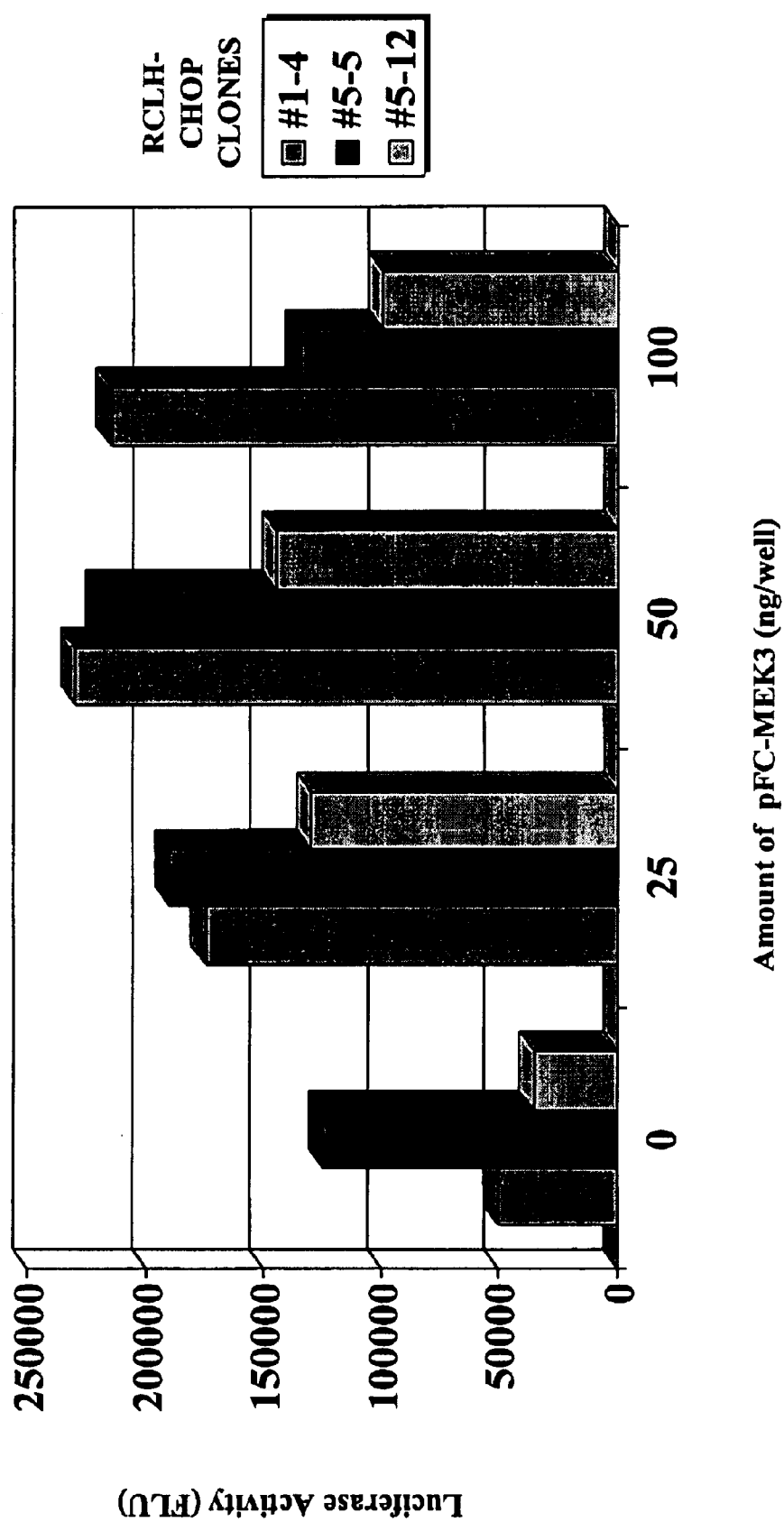

FIG. 8. Initial screening of RCLH-CHOP clones.

Cells (~3×10$^5$ per well) from various RCLH-CHOP cell clones were transfected with varying amounts of pFC-MEK3 activator plasmid. Luciferase activity in the cells was determined forty eight hours after transfection.

Figure 9:
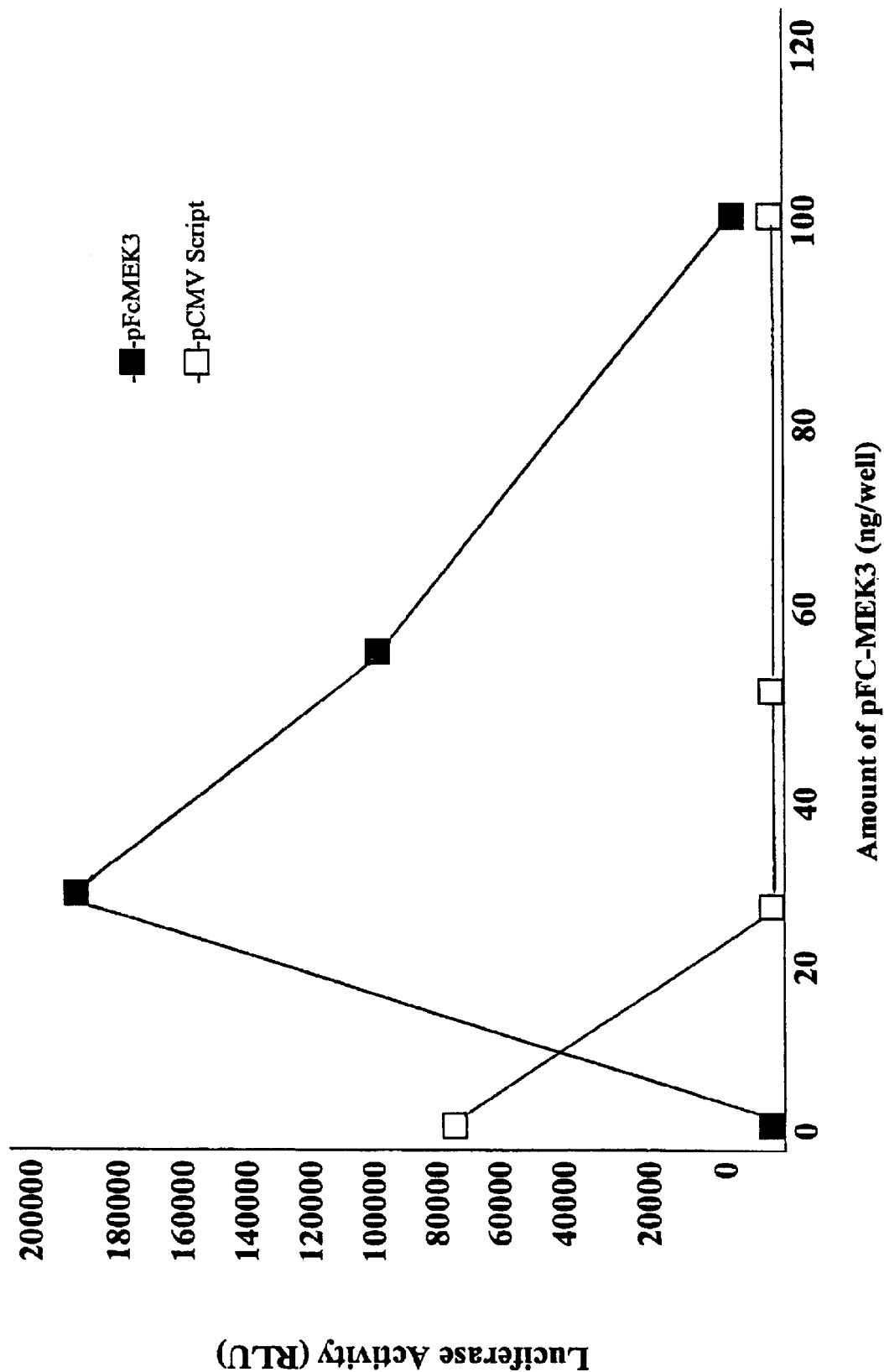

FIG. 9. Activation of luciferase expression by MEK3 in RCLH-CHOP cells.

RCLH-CHOP clone #1–4 cells (~3×10$^5$ per well) were trransfected with varying amounts of pCMVScript (open squares) or pFC-MEK3 (solid squares). DNA amounts of all samples were normalized with an unrelated plasmid (pBluescript). Luciferase activity in the cells was determined forty eight hours after the transfection. Luciferase activity from the zero point of pCMVScript (open square on the Y axis is an anomalous data point, as it was not observed in other experiments.

Figure 10:
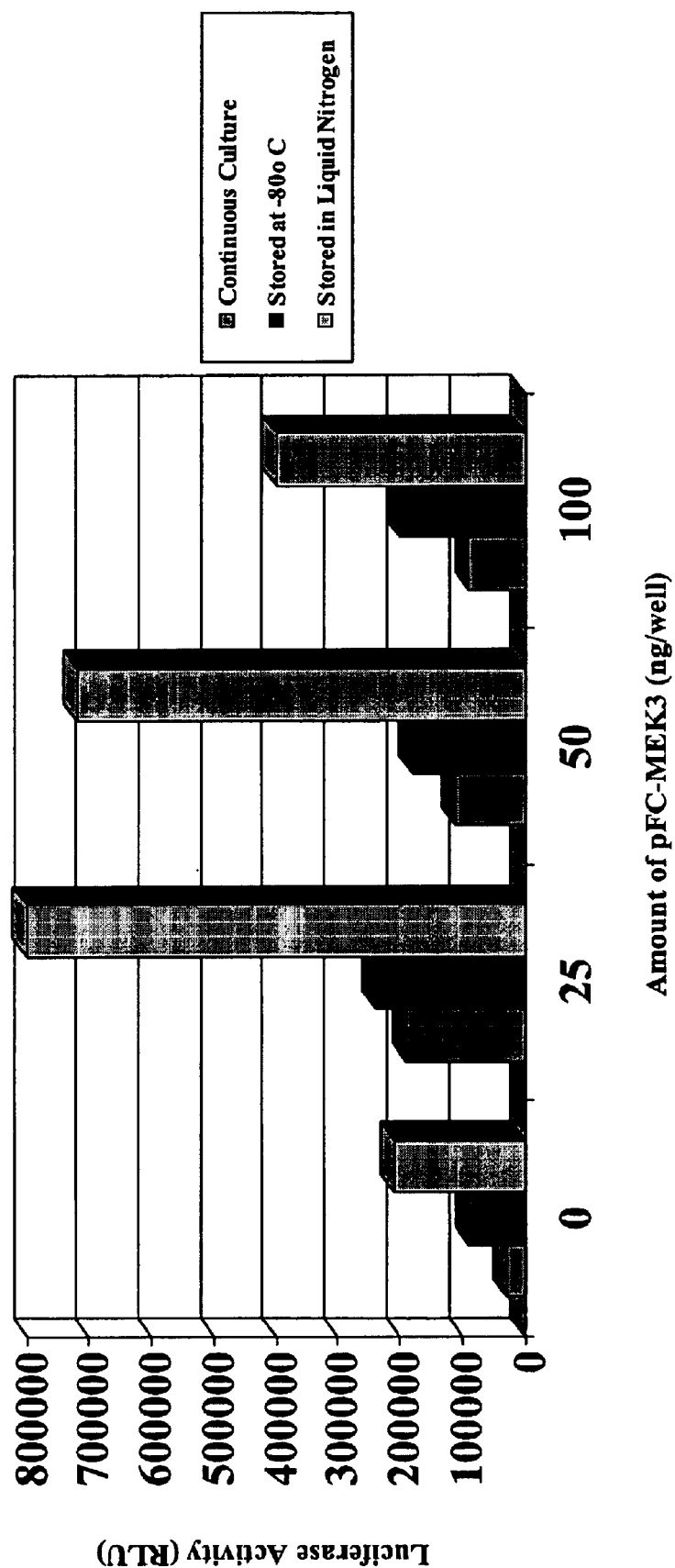

FIG. 10. Stability of RCLH-CHOP cell lines.

RCLH-CHOP clone #1–4 cells (~3×10$^5$ per well) were transfected with various amounts of pFC-MEK3 as indicated on the X axis. Luciferase activity in the cells was measured forty-eight hours after transfection. The cells have either been continuously cultured (blank bars), stored at −80° C. (shaded bars) or stored in liquid nitrogen (solid bars) for a period of over three months.

DETAILED DESCRIPTION OF THE INVENTION

The present invention addresses the need in the art for assay systems designed to provide consistent results in analyses of the CHOP pathway of signal transduction. The cell lines and assay systems disclosed herein are well suited for use in CHOP signal transduction pathway-specific assays to screen for candidate modulators of those signal transduction pathways, as well as for the study of transcriptional regulatory mechanisms in mammalian cells.

The invention relates to a cell line comprising a stably integrated recombinant nucleic acid construct comprising a reporter gene operably linked to a recognition sequence for a sequence-specific DNA-binding protein that responds to the activation of CHOP signal transduction.

The invention also relates to a cell line comprising a stably integrated recombinant nucleic acid construct comprising a reporter gene operably linked to a recognition sequence for a sequence-specific DNA-binding protein, and further comprising a stably integrated nucleic acid construct comprising a sequence encoding a transactivator fusion protein, such fusion protein comprising a DNA binding domain, wherein the DNA binding domain specifically binds the recognition sequence for a DNA binding protein operably linked to the reporter, and a conditionally active CHOP transactivation domain, wherein binding of the fusion protein to the recognition sequence results in transactivation of the reporter gene when the conditionally active CHOP transactivation domain fused to the DNA binding domain is activated.

As used herein a "conditionally active transactivation domain of CHOP" encompasses amino acids 1–101 of the transcription factor CHOP. Specifically, the conditionally active transactivation domain of CHOP comprises the amino acid residues:

NH$_3$-MAAESLPFTLETVSSWELEAWYEDLQEV-
LSSDEIGGTYISSPGNEEEESKTFTTLD-
PASLAWLTEEPGPTEVTRTSQSPRSPDSSQSSMA-
QEEEEEQG-COOH (SEQ ID No. 3)

and analagous sequences of transcription factor CHOP (for example, sequences that contain amino acid additions, insertions, deletions, substitutions) or other variations of CHOP that permit the protein or domain thereof to retain function as a conditionally active transactivation domain.

In one embodiment of the invention, a cell line is generated which carries one or more stably integrated copies of a reporter gene operably linked to at least one copy, preferably at least two copies or more, up to as many as five copies or more of the recognition sequence for the DNA binding domain of a sequence-specific DNA binding protein. A cell line of this type will be referred to herein as a reporter cell line.

As copies of a reporter plasmid (e.g., the luciferase reporter plasmid pFR-Luc) and an CHOP fusion transactivator plasmid are integrated into the chromosomes and become part of the genome in a reporter cell line (e.g., RCLH-Luc), the expression of reporter from them is subjected to many regulatory mechanisms unique to the natural state of genes on a chromosome. Stable integration of nucleic acids encoding reporters and CHOP transactivator fusion proteins improves the consistency and simplicity of assays for CHOP signal transduction beyond that of transient transfection systems and facilitates high-throughput applications. Using the resulting single or double stably transfected reporter cells, the effects of extracellular stimuli on signaling pathways converging at CHOP transactivating protein can be directly assessed by reporter assays without the need for transfection. These cell lines can also be used to study transcription mechanisms, and may be adapted for high-throughput drug screenings and panel assays. Therefore, the cell lines are useful tools for studying the regulation of the transcription machinery in vivo and to probe the roles of chromosomal structure in gene expression control.

CHOP Reporter Cell Lines Useful According to the Invention

A reporter cell line may be established from any desired eukaryotic cell line, preferably a mammalian cell line and not a yeast cell. A human cell line is of particular interest according to the invention. Methods of creating cell lines are well known in the art, and methods of creating stably transfected cell lines bearing at least one or more integrated constructs are also known in the art. Detailed descriptions of the various aspects of CHOP reporter cell lines according to the invention are presented below.

A. Parent Cell Line.

In order to be useful as a parent cell line according to the invention, the cell line should contain the protein kinases that activate the fusion transactivation protein. In other words, the CHOP pathway should be functional in the chosen cell type. Cell lines vary in signaling proteins and other properties. The endogenous protein kinases and transcriptional activator activities in the cell line will determine the background, and hence, the sensitivity of the assay. Further, the parental cell line must clearly be both transiently and stably transfectable, as readily determined by one skilled in the art. See Tables I and II for examples of experimental approaches to determine the activity of a pathway and reporters in a given cell line.

The examples described herein refer to the use of HeLa cells (ATCC #CCL-2) as the parental cell line. This should in no way be construed as limiting the invention to the use of HeLa cells.

B. Reporter Genes and Reporter Gene Expression Assays.

Reporter genes and assays for the expression of the reporter genes are widely known in the art. In order to be useful according to the invention, a reporter gene must have the following properties: i) its product (either nucleic acid transcript, protein, or protein activity) should be readily detectable; and ii) a reporter and detection system should preferably be amenable to high throughput applications. Another property to consider when choosing a reporter system is the stability of the product (Thompson et al., 1993, *Gene* 103: 171–177). Depending upon the exact use, one may wish to use a reporter whose measurable product has relatively high stability in the cell. Use of a stable reporter product will allow sensitive detection of pathway activity in terms of on versus off status; an example of a relatively stable reporter is the chloramphelicol acetyltransferase (CAT) gene product. However, in cases in which one wishes to detect changes such as a decrease in reporter gene activity, a relatively less stable reporter gene product or activity would be more desirable since it would more rapidly read out decreases in expression; an example of a relatively less stable reporter gene product is firefly luciferase. Reporter genes of use in the invention include, but are not limited to those encoding firefly luciferase (deWet et al., 1987, *Mol. Cell. Biol.* 7: 725–737) or luciferase genes from other species), -galactosidase, CAT and green fluorescent protein (GFP). Constructs encoding such reporter molecules are widely commercially available or may be obtained from sources such as ATCC.

In order to be useful for pathway-specific signal transduction assays, a reporter cell line (or a cell line bearing a reporter and a DNA binding domain:conditionally active transactivation domain fusion protein, referred to herein as pathway-specific reporter cell lines) must exhibit low background reporter activity in the absence of an activating signal. The definition of a low background level of reporter activity is clearly relative. What is important is that the level of reporter activity is sufficiently low that increases of one or more orders of magnitude may be detectable within the assay parameters when reporter gene activity is induced. Generally, one should avoid background levels wherein a tenfold or higher level of subsequent induction would saturate the assay (i.e., result in a non-linear signal response). When comparing a number of single or double stably transfected cell lines, it will be clear to one of skill in the art which one has the lowest background expression of reporter in the absence of an activating signal.

A strong reporter response upon treatment to activate the activator fusion will also be clear to one of skill in the art, particularly when comparing a number of singly or doubly transfected cell lines. It should be noted that while low background and strong response to activating signals are the desired ideals, the cell line with the lowest background will not necessarily be the line with the strongest response to activators. It is within the ability of one of ordinary skill in the art to choose a reporter cell line, from among a number of given reporter cell lines, which has the optimal balance of low background and strong responsiveness to activator treatment.

Reporter gene expression may be assayed according to standard methods known in the art and appropriate for the chosen reporter gene.

While the invention is not intended to be limited to using a particular reporter, firefly luciferase is well suited for the methods of the invention. In the assays shown in subsequent Examples, cell lysates were prepared and tested for luciferase activity using the Luciferase Assay Kit (Stratagene) according to manufacturer's specifications (Further information regarding luciferase assay methods may be found in Brasier, et al., 1992, Methods Enzymol. 216: 386–97). Typically, cells were lysed with 100 ul of lysis buffer (40 mM Tricine (pH 7.8), 50 mM NaCl, 2 mM EDTA, 1 mM $MgSO_4$, 5 mM Dithiothreitol (DTT), and 1% Triton X-100) and 20 ul were used per assay. Lysis may alternatively be performed by freeze-thaw, although this method is known to reduce luciferase activity by as much as 50% per cycle. Cell lysate was mixed with 100 ul of luciferase assay reagent (40 mM Tricine (pH 7.8), 0.5 mM ATP, 10 mM $MgSO_4$, 0.5 mM EDTA, 10 mM DTT, 0.5 mM coenzyme A, 0.5 mM luciferin) in a Falcon 2054 tube, and relative light units were measured in a single tube luminometer (Tropix) using an integration time of 15 seconds. Longer integration times may be used if necessary. For high throughput screening applications, an automated reporter assay method may be preferable.

C. Promoters Useful According to the Invention.

The promoter used in the reporter gene construct can be any promoter operative in the signal transduction pathway, but is preferably a minimal promoter. That is, the promoter will contain a TATA element linked to the coding sequence for the reporter (see, for example, FIG. 4). The one or more DNA-binding domain recognition sequence elements may be linked, preferably 5', but possibly also 3' of the reporter coding sequence. The reporter coding sequence may include one or more introns. One of skill in the art may readily determine whether the reporter construct exhibits low background expression and is induced by recruitment of a transactivation domain to the DNA-binding domain recognition sequence element(s). Activation may be tested, for example, by transient transfection with a complete transactivator protein (that is, one containing both an activation domain and the appropriate DNA-binding domain), preferably one with constitutive activity. Activation may also be tested by transfection with a native, conditionally active transactivator protein in the presence of an appropriate activator.

D. DNA Binding Domains of Use According to the Invention.

A sequence-specific DNA binding domain may be either known in the art or may be identified in a native (i.e., functionally intact as it occurs in nature) sequence-specific transactivator protein by one of skill in the art through systematic deletion mutagenesis of a cloned native sequence-specific transactivator protein. Deletion mutants may be expressed in mammalian or other cells either alone or as fusions with another non-DNA-binding protein (e.g., glutathione-S-transferase) and screened for retention of DNA binding using electrophoretic mobility shift assays with a DNA probe comprising the sequence recognized by the native protein as known in the art. Deletion mutants that retain specific DNA binding activity may then be screened in transient transfection assays for their ability to transactivate a reporter gene operably linked to one or more copies of the recognition sequence bound by the native transactivator protein. To be useful in the cell lines and methods of the present invention, the identified DNA binding domain should retain sequence-specific DNA binding activity but lack transactivation activity on its own. Non-limiting examples of DNA binding domains useful in the invention include GAL4 amino acids 1–147 and LexA amino acids 1–87.

It is well within the ability of one skilled in the art to generate fusion proteins as called for within the invention.

E. Conditionally Active Transactivation Domains of Use According to the Invention.

Generally, a conditionally active transactivator fusion protein is one that comprises the transactivation domain of a conditionally active transcription factor (e.g., CHOP). Such a transcription factor must participate in the signal transduction pathway one wishes to monitor. Most commonly, a conditionally active transactivation domain is regulated by modification such as phosphorylation or dephosphorylation, although other activating mechanisms, such as association or dissociation of a regulatory factor with a conditionally active transactivating factor (for example, inhibitory factor IkB association with NF-KB p65), increased DNA binding affinity induced by a conformational change, inducible nuclear localization (for example, nuclear translocation of NFAT proteins after dephosphorylation by clacineurin) or proteolysis (for example, cleavage of inactive precursor such as NF-kB p 105 to generate an active p50 NF-kB p50 subunit) also exist. It is important that the DNA-binding domain-transactivator fusion protein does not activate transcription in the absence of a factor or signal which activates the conditionally active transactivator domain. This conditional activity makes the DNA-binding domain-activator fusion protein particularly useful according to the invention. A DNA-binding domain-transactivator fusion which is only active when stimulated by signaling proteins in the specific pathway being examined (e.g., the CHOP pathway) will reliably read out the activity of the particular signal transduction pathway by stimulation of reporter gene activity.

To be chosen for use in the cell lines and methods of the invention, it is assumed that the conditionally active, pathway-specific transactivation domain, such as CHOP amino acids 1–101 is known to be conditionally active and pathway specific. A particular conditionally active transactivation domain may be identified within a conditionally active transactivator protein through systematic deletion mutagenesis as follows. A nucleic acid sequence encoding the entire transactivator protein or portions thereof may be fused in-frame with a sequence encoding a sequence-specific DNA-binding domain. A panel of systematic deletion mutants (generated according to any one of several methods known in the art) may then be tested for transactivation activity by cotransfecting them along with a reporter gene construct bearing linked copies of the DNA-binding domain recognition sequence in the presence of an activating signal for the conditionally active transactivating protein. The smallest portion of the conditionally active transactivator protein found to retain transactivating activity identifies the transactivation domain. One of skill in the art may determine by incubating transfected cells in the presence and absence of an activating signal (a chemical or a co-transfected upstream activator) for the transactivation domain whether the identified transactivation domain retains its conditional activity. A conditionally active transactivator will induce reporter gene expression in this assay only in the presence of such a specific activator of the transactivation pathway.

It is preferred that the conditionally active transactivator fusion protein be constitutively expressed. In this way, differences in reporter activity accurately reflect differences in pathway activity, rather than differences in activator expression. Under some circumstances, however, it may be desirable to express the activator fusion from a tissue- or cell type-specific promoter, or from an inducible promoter. The use of a cell type-specific promoter may, for example, ensure higher expression of stably integrated copies of the activator fusion protein. For example, if liver-derived cells are to be used, one may prefer to use a liver-specific promoter, such as the albumin or alphafetoprotein promoter to drive high level expression of the fusion activator.

F. Transactivator Fusion Protein Expression Constructs.

The CHOP transactivator fusion protein sequence may be included in any one of a variety of expression vectors. It is necessary that the vector chosen is capable of chromosomal integration; i.e., the chosen vector should not carry signals promoting episomal maintenance. Any plasmid or vector meeting this condition and being replicable in the chosen host cell without harming the viability of the host cell is acceptable according to the invention.

The conditionally active CHOP transactivator fusion protein construct may include sequence encoding a leader sequence that may be cleaved by the host cell to generate the mature form of the polypeptide. In addition, the encoded CHOP transactivator fusion protein may contain a prosequence, which is the mature protein plus additional amino-terminal amino acid residues. A mature protein having a prosequence is a proprotein and may in some cases be an inactive form of the protein. Once the prosequence is cleaved an active mature protein remains. Thus, for example, the transactivator fusion protein of the invention may be encoded by a nucleic acid construct encoding a mature protein, a protein having a prosequence or a protein having both a presequence (leader sequence) and a prosequence.

As herein above indicated, the CHOP transactivator fusion protein DNA sequence may be inserted into the vector by a variety of procedures. In general, the DNA sequence is inserted into appropriate restriction endonuclease sites by procedures known in the art. Such sites may be existing sites or sites created or modified according to methods known in the art. Specific information on methods involved in cloning and mutagenesis may be found, for example, in Ausubel et al. (Ausubel et al., 1988, *Current Protocols in Molecular Biology*, (John Wiley and Sons, Inc.)) and in Sambrook et al. (Sambrook et al., *Molecular Cloning: A Laboratory Manual*, Second Edition, 1989, (Cold Spring Harbor Press, Cold Spring Harbor, N.Y.)).

The DNA sequence in the CHOP transactivator fusion protein expression vector is operatively linked to an appropriate, preferably eukaryotic (or at least functional in eukaryotic cells) expression control sequence (promoter) to direct mRNA synthesis. An appropriate control sequence is one which directs expression of the linked construct in the chosen cell type. Examples of such promoters include but are not limited to viral control sequences (e.g., retroviral LTRs, SV40 promoter, Adenoviral promoters, CMV promoter, HSV promoter, etc.) and promoters for eukaryotic cellular genes such as the mouse metallothionein promoter, housekeeping gene promoters such as GAPDH, or even tissue-specific promoters such as the albumin or immunoglobulin promoters.

Transcription of a DNA construct encoding the CHOP transactivator fusion protein may be increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

The CHOP transactivator fusion protein expression vector also contains a ribosome binding site for translation initiation and a transcription terminator. The vector may also include appropriate sequences for amplifying expression. The expression vector may additionally be regulated in an inducible manner, such as by addition (or removal) of a chemical regulator (e.g., IPTG, tetracycline), by co-expression of an inducer or repressor (e.g., lac repressor, ecdysone receptor) or by other means known in the art.

Selectable markers generally fall into one of two groups that differ in the manner of selection. The first group, the recessive markers, are usually genes that encode products that are not produced in the host cells. Recessive markers include genes for thymidine kinase (TK), dihydrofolate reductase (DHFR), adenine phosphoribosyl transferase (APRT), and hypoxanthine-guanine phosphoribosyl transferase (HGPRT). The second group, the dominant markers, includes genes that encode products conferring resistance to growth-suppressing compounds (antibiotics, drugs) and/or permit growth of the host cells in metabolically restrictive environments. Commonly used dominant markers include a mutant DHFR gene that confers resistance to methotrexate; the gpt gene for xanthine-guanine phosphoribosyl transferase, which permits host cell growth in mycophenolic acid/xanthine containing media; the neo gene for aminoglycoside 3'-phosphotransferase, which can confer resistance to G418, gentamycin, kanamycin, and neomycin; and the hygromycin resistance gene.

For more information regarding expression vectors active in mammalian cells, see, for example, Kaufman, 1990, *Meth. Enzymol.* 185:487–511.

G. Nucleic Acid Constructs and Methods of use in the Invention.

1. Plasmids

Fusion transactivator plasmid pFA2-CHOP is available from Stratagene. The fusion transactivator plasmid was made by introducing sequences coding for CHOP amino acids 1–101 in frame into the plasmid pFA-CMV. See FIG. 5 for a schematic representation of the fusion transactivator plasmid, and FIG. 6 for a schematic representation of the pFA-CMV backbone plasmid which carries the sequences encoding the GAL4 DNA binding domain (amino acids 1–147) linked to a multiple cloning site. Any conditionally active transactivation domain may be expressed as a GAL4 fusion by introducing the nucleic acid sequence in frame to the multiple cloning site of the pFA-CMV plasmid by methods known in the art. pFA-CMV further encodes the neomycin resistance gene selectable marker.

To facilitate the integration and selection for stable reporter gene integration, a hygromycin resistance expression cassette, excised from p3'SS (a vector for LacSwitch™ expression systems (Stratagene, GenBank Accession No. U42371), was inserted into the NdeI site of the pFR-Luc (Genbank Accession No. AF058756) luciferase reporter vector, to generate pFR-Luc-Hyg. pFR-Luc (and therefore pFR-Luc-Hyg) carries five copies of the GAL4 DNA-binding domain recognition sequence 5'-CGGAGTACTGTCCTCCG-3' (SEQ ID No. 4) upstream of a basic TATA element and the coding region for firefly luciferase (see FIG. 4).

Control plasmids of use in the invention include but are not limited to a construct encoding a GAL4 DNA-binding domain alone (e.g., pFC2-DBD), and an expression construct for MEK3 (pFC-MEK3), for use as upstream activators (see FIG. 7). These plasmids are available from Stratagene.

Plasmid DNAs used for transfection were purified from *E. coli* XLI-Blue cells (Stratagene) with Qiagen maxi prep kits or by CsCl banding. Clearly, one of skill in the art may prepare plasmid DNAs using other strains of *E. coli* or other bacteria as known in the art.

2. Preparation of Genomic DNA

Genomic DNAs from cultured cells were prepared using Stratagene's DNA Extraction Kit (Cat#200600) according to the instruction manual using $4 \times 10^6$ cells. Alternatively, other methods known in the art may be applied in order to isolate genomic DNA from cultured cells (See, for example, Maniatis et al., 1982, *Molecular Cloning: A Laboratory Manual*, Cold Spring Harbor Press, Cold Spring Harbor, N.Y., p. 280).

3. Cell Culture

HeLa cells were kept and cultured in DMEM, 1% L-Glutamine supplemented with antibiotic/antimycotic liquid (Gibco BRL) and 10% fetal bovine serum (Hyclone or Gemini), according to standard protocols. Other established cell lines (as available from various commercial sources, or, for example, from American Type Culture Collection, Manassas, Va.) may be cultured according to the conditions published for such lines or as determined by one of skill in the art. Cell lines for use in the invention may be derived from any eukaryote, preferably a mammal, and more preferably a human.

4. Transient Transfection

Transfections were performed in 24 well dishes using LipofectAMINE™ (Life Technologies) or LipoTaxi™ (Stratagene) following manufacturer's guidelines (other companies offering lipid-mediated transfection reagents include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA). Briefly, cells were seeded at $5 \times 10^4$ cells per well and incubated overnight at 37° C. DNA lipid mixtures were prepared according to manufacturer's recommendations, incubated at room temperature for 20–40 minutes and overlaid onto the cells (0.25 ml per well). Equal volume of medium containing 1% fetal bovine serum was added to each well 5 hours after transfection. Medium was replaced 18–24 hours post transfection with fresh DMEM containing 0.5% fetal bovine serum. Cell lysates were collected 48 hours after transfection and assayed for luciferase activity.

Transient transfections may also be performed using the calcium phosphate precipitation, electroporation or DEAE dextran methods as known in the art (Ausubel et al., 1992, *Short Protocols in Molecular Biology* (John Wiley & Sons, NY), pp. 9–5 to 9–14).

5. Determination of Stable Integration of Transfected Constructs

Stable integration of transfected constructs may be determined using PCR and genomic cellular DNA (Mullis &

Faloona, 1987, *Methods Enzymol.*, 155:335). To ascertain reporter integration, PCR primers corresponding to the linked recognition sequence for the DNA-binding domain and the reporter coding region are appropriate. Amplification of a band of the expected size following the selection protocol will verify the integration of one or more intact (that is, retaining the recognition sequence(s) and the reporter coding region) copies of the reporter construct. To assay for stable transfection with fusion transactivator constructs, one PCR primer should be specific for the fusion DNA-binding domain domain (e.g., GAL4, LexA, etc.) and the other should be specific for the fused transactivation domain.

H. Determining the Activation Status of a Transactivating Protein.

A stable reporter cell line stably transfected with a nucleic acid construct encoding a conditionally active CHOP transactivator fusion protein (that is, a pathway-specific reporter cell line) may be used to assay for the activation status of the conditionally active CHOP transactivation domain and/or the activation status of the signal transduction pathway of which the conditionally active CHOP transactivation domain is a participating member. Such an assay would comprise the step of performing a reporter gene expression assay on such double stably transfected cells. The detected reporter gene activity reflects the activation status of the conditionally active transactivator, and thus reflects the activation status of the signal transduction pathway.

A double stably transfected, CHOP pathway-specific reporter cell line may also be used to screen for a candidate modulator of the selected signal transduction pathway. Such an assay comprises the steps of incubating such a double stably transfected pathway-specific reporter cell line in the presence or absence of a candidate modulator compound and detecting reporter gene activity. A change or difference (increase or decrease) in the level of reporter gene activity in the presence of a candidate modulator compound relative to the expression in the absence of the candidate modulator compound is indicative of a modulatory effect of such a candidate compound. Such an assay performed in the absence of a known activating signal (i.e., a signal that activates the conditionally active transactivation domain on the fusion transactivator) may be used to screen for an activator of the signal transduction pathway. Alternatively, an assay performed in the presence of a known activating signal may be used to screen for either a further activating activity or for an inhibiting activity.

I. Activating Signals.

Activating signals may comprise chemical compounds known to specifically activate the specific signal transduction pathway being assayed (e.g., dibutyryl cAMP activation of the cAMP-dependent CREB pathway), or they may comprise treatments such as growth factor addition, thermal shock, induction of oxidative stress, or exposure to UV or other irradiation. Activating signals and treatments specific for particular signal transduction pathways are known in the art. In addition to activating signals or compounds known in the art, one may use an activating compound, identified by screening candidate compounds in a pathway-specific reporter cell line in the absence of a known activating signal, as described in the previous section.

Alternatively, an activating signal may comprise a treatment of the reporter cell line that induces the expression of an upstream activator of the signal transduction pathway being studied. Such an upstream activator may be, for example, a regulatory kinase (e.g., MEK3) acting upstream of the activator used as the fusion activator (e.g., CHOP). In this instance, a nucleic acid construct encoding an upstream activator may be transfected, either transiently or stably (under control of an inducible promoter), into the reporter cell line. The expression of an upstream activator from a transiently-transfected activator construct or from a stable, indicible upstream activator construct will then induce the activity of the signal transduction pathway being studied. The upstream activator may be expressed in either its native form, or, alternatively, as a constitutively active mutant form. Inducible expression systems are well known in the art; non-limiting examples include those induced by heat, the presence or absence of an antibiotic (e.g., tetracycline) or hormone (e.g., ecdysone), or the presence of activators such as IPTG (e.g., the LacSwitch™ system; Stratagene).

As another alternative, an activating signal may be provided in the form of a transfected, conditionally active upstream activator protein. In contrast to the situation in which expression of an upstream activator is induced, in this case the activity of the upstream activator is conditionally induced. Examples include temperature sensitive mutants of upstream activators, e.g., p53. A temperature shift results in a conformational change in the factor that activates or inactivates the upstream activator (see, for example, Milczarek et al., 1999, *Carcinogenesis* 20: 1043–8).

J. Candidate Modulators According to the Invention:

A "candidate modulator" as used herein, is any compound with a potential to modulate the activity of the CHOP signal transduction pathway.

A candidate modulator is tested in a concentration range that depends upon the molecular weight of the molecule and the type of assay used. For example, for inhibition of transcription initiation, protein/DNA or protein/protein complex formation, small molecules (as defined below) may be tested in a concentration range of 1 pg–100 g/ml, preferably at about 100 pg–10 ng/ml; large molecules, e.g., peptides, may be tested in the range of 10 ng–100 g/ml, preferably 100 ng–10 g/ml.

Inhibitors of specific signal transduction events may target a protein factor that interacts with regulatory factors so as to prevent or enhance the natural biological interaction that occurs in vivo which leads to transcription. As another alternative, a candidate modulator may directly affect the activity of a particular signal transduction pathway protein. Thus, a modulator of a signal transduction pathway identified as described herein will possess two properties: 1) at some concentration it will modulate the activity of a factor which is related to a specific signal transduction pathway; and 2) at the same concentration, it will not significantly affect the expression or function of unrelated factors.

Candidate modulators will include peptide and polypeptide inhibitors having an amino acid sequence based upon the components of the protein participating in the specific signal transduction pathway. For example, a mutant of a signal transduction protein factor, or a fragment of a mutant or wild-type protein, may act as a competitive inhibitor with respect to the activity of the factor. Alternatively, a mutant or fragment of the protein may be engineered such that it instead enhances the activity of the signal transduction factor. This may be achieved through enhanced binding affinity to either its protein binding partners or through constitutive, rather than regulated activity.

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds are readily modified through conventional chemical, physical, and biochemical means.

Useful compounds may be found within numerous chemical classes, although typically they are organic compounds, and preferably small organic compounds. Small organic compounds have a molecular weight of more than 50 yet less than about 2,500 Daltons, preferably less than about 750, more preferably less than about 350 Daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability such as: using an unnatural amino acid, such as a D-amino acid, particularly D-alanine; functionalizing the amino terminus, e.g. by acylation or alkylation; functionalizing the carboxylic terminus, e.g. by esterification or amidification; or the like.

A candidate modulator of the activity of the CHOP signal transduction pathway, assayed as described herein, is determined to be effective if its use results in a change or difference of about 10% or greater of signal detected in the reporter assay.

The level of modulation by a candidate modulator may be quantified using any acceptable limits, for example, via the following formula. The calculations are the same when luminescent, calorimetric, fluorescent, radioactive or other detection methods are utilized.

$$\text{Percent Modulation} = \frac{(\text{Control signal} - \text{Sample signal})}{(\text{Control signal})} \times 100$$

where "Control signal" is the average of the reporter activity detected in assays that lack the candidate modulator (in other words, untreated controls), and "Sample signal" is the reporter activity detected in assays containing the candidate modulator. A similar calculation is appropriate whenever the assay yields a linear relationship between the amount of signal detected and the amount of protein or nucleic acid being represented per unit of signal or the amount of protein or nucleic acid represented by a unit of enzymatic activity.

How to Make a CHOP Reporter Cell Line According to the Invention

A CHOP reporter cell line is established by transfecting a reporter construct and a conditionally active CHOP transactivator fusion construct into a parent cell line, and selecting for clones that have integrated both the reporter and the fusion activator constructs. Clones are analyzed for background expression levels of the reporter, inducible expression of the reporter with stimuli specific for the pathway of interest, and for the phenotypic stability of the transreporting system. The primary criteria for choosing a stably transfected clone for use in the methods of the invention include stable chromosomal integration of the reporter construct, stable integration of the conditionally active fusion transactivator construct, low background of Luc or other reporter activity in the absence of activating signals, and strong, preferably dose-dependent induction of reporter activity upon treatment of cells to induce the activation of the fusion transactivation domain. The details of the establishment and evaluation of stably transfected reporter cell lines according to the invention are presented as follows.

A. Establishment of Stably Transfected CHOP Reporter Cell Lines.

Stable transfection methods are widely known in the art. Essentially, DNA is introduced to the cells by the same procedures used for transient transfection, e.g., cationic liposomes (such as LipofectAMINE™ (Life Technologies)), electroporation, calcium phosphate precipitation or DEAE dextran, followed by selection with a selection agent for that small proportion of the cells which integrate the introduced construct(s) into their chromosomes. Selection for stable transfectants is performed using a selection agent compatible with the selectable marker(s) on the plasmid(s) one desires to stably integrate.

1. Transfection and selection for stable integration.

When two different constructs are to be stably integrated, they may be either simultaneously transfected and selected for with two selection agents, or they may be sequentially transfected, selecting for clones (or pools of clones) integrating at least one copy of one construct, followed by transfection of those clones or pools of clones with the second desired construct. Because of the relatively low occurrence frequency of stable integration events, it is often, although not always, found that the sequential approach is more effective in obtaining double stable transfectants.

A sample transfection scheme is outlined below.

Day 1: Plate cells in 100 mm tissue culture dishes ($5 \times 10^5$ cells per dish).

Day 2: Transfect cells using the Mammalian Transfection Kit (Stratagene), with 1–10 ug of plasmid DNA per transfection as follows:
  a) prepare a DNA-lipid complex according to the instructions supplied by the manufacturer of the polycationic liposome transfection kit;
  b) dilute the DNA-lipid complex to a final volume of 3 ml with serum-free medium;
  c) rinse the cells with serum-free medium;
  d) mix gently and overlay 1 ml of the diluted DNA-lipid complex onto the cells;
  e) incubate the cells with the DNA-lipid complex for 5–7 hours (this is an estimate; the time of exposure of cells to lipid-DNA complex will vary with cell type and the exact amount and ratio of DNA and lipid; one of skill in the art may determine the optimal amounts of DNA and lipid, the optimal duration of cell exposure, as well as whether medium should be supplemented with small amounts of serum during the exposure of cells to the DNA-lipid complex, through a series of preliminary experiments wherein each variable is systematically varied while all others are held constant; determinations of this kind are routine in the field);
  f) rinse off the DNA-lipid complex and add complete non-selective medium.

Day 3: Wash cells twice with PBS. Add fresh non-selective medium.

Day 4: Split cells 1: 10–1:80 into 100 mm petri dishes.

Day 5: Change to selective medium containing selective agent (e.g., 0.5 mg/ml hygromycin or 0.2 mg/ml G418; amounts may be varied depending on the sensitivity of a given cell line to the chosen selective agent(s) as determined by one of skill in the art).

Day 15: (14–20 days are required for single, well-isolated colonies to be visible) Single colonies are lifted from the plates using small pieces of sterile filter paper saturated with Trypsin/EDTA. Single colonies are transferred to 24-well plates. As these wells become confluent, the clones are expanded to 12-well, and then 6-well plates, and finally to T-25 tissue culture flasks. At this point the selective pressure may be reduced by 50% (0.25 mg/ml G418 and/or 0.1 mg/ml hygromycin). The clones are then tested by transient transfection and, if positive, frozen for storage.

Stable integration of the reporter and CHOP fusion transactivator plasmids is determined by PCR amplification of a band of the expected size using primers specific for portions of the transfected constructs as described herein.

Resulting stable colonies are picked and screened to determine background expression of the reporter, and to evaluate the response of the reporter to expression of transactivators or fusion transactivators. Clones that demonstrate the strongest responses may then be tested more extensively.

2. Evaluating the function of stably integrated constructs.

Clones with integrated reporter and CHOP fusion transactivator constructs must be functionally evaluated with regard to the pathway-specific reporting system. Specifically, cells are evaluated for reporter background activity and for the response of the reporter to treatments that induce the CHOP pathway to which the reporter/fusion transactivator system is designed to respond.

Clones of cells bearing stably integrated reporter and CHOP fusion transactivator constructs are evaluated for background activity of the reporter by assaying the reporter in cells without any treatment to induce the activation of the fusion transactivation domain.

Doubly transfected clones exhibiting low background are then tested for the response of the reporter to activating signals. Activiating signals may be any of those discussed in the section "Activating Signals" above, including, but not limited to growth factors, cytokines, chemical agents (such as cycloheximide or PMA), treatments such as UV or other irradiation, treatments that induce thermal, oxidative, or hypoxic stress, and expression of upstream activators. It is expected that the reporter in pathway-specific reporter cell lines will respond to only those activators that normally activate the pathway the cells were designed to monitor, e.g., the CHOP pathway. Assays with activating signals may be performed with varying doses or amounts of the activating signal to monitor the dose-dependence of the reporter response.

B. Assessing the Stability of Stably Transfected Constructs.

The phenotypic stability of the integrated construct(s) in cells of the invention may be assessed by treating cells from a given clone as follows: one group of cells from a clone may be continuously maintained in culture (under selective pressure, such as 50% of the level of selective agent(s) used in the original selection for the clones) for two months; another group may be subjected to the cycle of freezing, storage at −80C., thawing and reculturing at least two times during a two month period; and a third group may be frozen and thawed as was the second group, except with storage under liquid nitrogen. Cells treated in this manner are then tested for reporter expression in response to transient transfection with upstream activators (e.g., MEK3) and/or in response to extracellular stimuli such as UV, TNF-or oxidative. Cells that continue to exhibit a reporter response to such activating treatments after the various storage and culture regimens are considered to have a stable phenotype according to the invention.

C. Selection of Stably Transfected Reporter Cell Lines Using HeLa Cells as the Parental Cell Line.

The CHOP trans-reporting system described herein has been tested by transient assays in HeLa cells. As such, the HeLa cell line was used as a parent cell line to establish stable reporter cell lines. HeLa cells cultured as described above were stably transfected as follows (this scheme is similar for both single and double transfectants, with the difference being that double transfectants are selected with two selective agents, instead of one as used for single transfectants):

Day 1: Plate cells in 100 mm tissue culture dishes ($5 \times 10^5$ cells per dish).

Day 2: Transfect cells using the Mammalian Transfection Kit (Stratagene), with 1–10 ug of plasmid DNA per transfection.

Day 3: Wash cells twice with PBS. Add fresh non-selective medium (or, for cells already bearing a single stable construct and being transfected with a second construct, add fresh medium supplemented with only the selective agent for the first construct).

Day 4: Split cells 1:10–1:80 into 100 mm petri dishes.

Day 5: Change to selective medium containing 0.2 mg/ml hygromycin.

Day 15: (14–20 days are required for single, well-isolated colonies to be visible) Single colonies were lifted from the plates using small pieces of sterile filter paper saturated with Trypsin/EDTA. Single colonies were transferred to 24-well plates. As these wells became confluent, the clones were expanded to 12-well, and then Swell plates, and finally to T-25 tissue culture flasks. At this point the selective pressure was reduced by 50% (0.25 mg/ml G418 and/or 0.1 mg/ml hygromycin). The clones were then tested by transient transfection and, if positive, frozen for storage.

After transfection of HeLa cells with pFR-Luc-Hyg, a total of 11 hygromycin-resistant clones were selected and tested for reporter activity. Resulting stable colonies were picked and screened in transient transfection assays. One clone, #1C3, showed very low background reporter expression, but was highly responsive to transient transfection with plasmid pFC-MEK3 (data not shown). Therefore, clone # 1 C3 was selected for later use and designated RCLH-Luc (for reporter cell line derived from HeLa containing luciferase). All of the stable, doubly transfected cell lines containing both pFR-Luc and the fusion transactivator vector pFA2-CHOP (see below) were established by transfecting the latter plasmid into the RCLH-Luc reporter cell line.

D. Establishment of RCLH-CHOP Cell Lines.

Several approaches were tried initially to simultaneously transfect both the reporter vector pFR-Luc-Hyg and the conditionally active, pathway-specific fusion transactivator vector pFA2-CHOP into HeLa cells. Only the sequential approach of transfecting cells already stably transfected with pFR-Luc-Hyg (I.e., RCLH-Luc cells) with the pFA2-CHOP plasmid vector and selecting with G418 (0.5 mg/ml) turned out to be successful (see FIG. 3 for a schematic of the approach taken in transfecting HeLa cells with the pFR-Luc reporter and the CHOP pathway fusion transactivator).

G418-resistant clones were screened for integration of the pFA2-CHOP construct by PCR, with one primer specific to the GAL4 DNA binding domain and the other to the CHOP transactivation domain. Detection of an amplified fragment of the expected size confirms the chromosomal integration of the pFA2-CHOP fusion transactivator construct.

The resulting clones containing integrated pFA-2 CHOP were initially screened by their response to the transiently transfected positive control upstream activator vector pFC-MEK3. A total of thirty-one G418 resistant clones were screened with assays similar to those shown in FIG. 8, and clone #14 was selected for further testing. Criteria for choosing clone #14 over the other cell lines include stable integration of pFR-Luc and pFA2-CHOP, low background of Luc expression in the absence of signals which activate the activator fusion protein, and strong, dose-dependent induction of reporter activity upon treatment of cells to induce the activity of the activator fusion protein.

The dose-dependence of RCLH-CHOP clone # 14 reporter activation was evaluated by transient transfection with varying amounts of pFC-MEK3 as shown in FIG. 9. RCLH-CHOP clone #14 exhibited a strong response with 25 ng/well of pFC-MEK3 expression plasmid, followed by a decline in activation at 50 and 100 ng/well, followed by Overexpression of a protein (e.g., MEK3) in the cell often gives rise to dramatic, but sometimes non-physiological results. The effect of extracellular stimuli affecting the CHOP pathway may be examined using RCLH-CHOP cell lines. For example, RCLH-CHOP cells may be treated with UV light or TNF-, which are known to activate the p38 MAPK/CHOP pathway, followed by luciferase assays. The response of the chromosomally integrated reporter to extracellular stimuli which activate the p38 MAPK/CHOP pathway indicates that the chromosomally integrated copies of the reporter and fusion transactivator constructs reconstitute the CHOP-specific reporter assay system in the RCLH-CHOP stable cells.

The phenotypic stability of the transreporting system in the RCLH-CHOP cells was evaluated as follows. RCLH-CHOP stable cell lines were either continuously cultured, stored at −80° C., or stored under liquid nitrogen for a period of over three months. Cells were then asayed for luciferase activity in response to pFC-MEK3 transfection. As shown in FIG. 10, cells retained responsiveness to transfected upstream activator. Storage in liquid nitrogen preserved the responsive phenotype, including the dose-responsiveness, to a greater extent than did the other storage or culture conditions. Nonetheless, the RCLH-CHOP reporter cell phenotype is stable.

It should be noted that the absolute level of reporter induction will vary depending upon the number of copies of integrated reporter and fusion transactivator plasmids. Transient transfection generally introduces more copies of the respective plasmids than are retained in stable cell lines. Therefore, the absolute reporter activity level obtained from stable reporter cell lines is generally lower than in similar transient assays. The fold activation, however, generally remains similar whether using transient or stable transfection, since transient assays have higher reporter background than do assays in stable cells.

Taken together, these results demonstrated that the chromosomally integrated copies of both pFR-Luc and pFA2-CHOP reconstitute the pathway-specific reporter assay system in the RCLH-CHOP stable cells, and that the system is phenotypically stable. Signal transduction pathways converging at the CHOP protein can be studied much more extensively, conveniently and consistently with RCLH-CHOP cells than with the transient system. As the name mitogenactivated protein kinase suggests, the MAPK pathway plays a pivotal role in normal, as well as abnormal, cell growth and differentiation. Many components along the pathway are known oncogenes and potential targets of various drug-screening efforts. Therefore, RCLH-CHOP cells will greatly enhance the ability to set up high throughput assays needed for drug (inhibitors) screening efforts and panel assays for possible carcinogenic activities (activators) of various commercial compounds.

Kits According to the Invention

In one embodiment of the invention, a single or double stably transfected reporter cell line may be assembled into a kit, such a kit allowing one to assay protein:protein interactions, the activity of specific signal transduction pathways, the activity of specific transactivating proteins or transactivation domains thereof and/or to screen candidate modulators of the activity of such pathways or transactivating proteins or domains thereof. A kit of this type will comprise a reporter cell line of the invention, packaging materials and instructions for the use thereof. A kit may additionally comprise activating signal compounds or nucleic acid constructs (such as those encoding activator- or DNA binding domain-fusion proteins or upstream activator proteins specific to a given signal transduction pathway) as described herein above.

The cell lines and methods of the invention are further described in the following non-limiting examples, and in the claims.

EXAMPLES

Example 1

Analysis of the Function of a Gene Product Using RCLH-CHOP Stable Reporter Cells To study the effect of a gene product on the CHOP signaling pathway using fusion transactivators, the gene of interest (i.e., a gene encoding a product that may regulate the specific signal transduction pathway) should be cloned into a mammalian expression vector such as pCMV-Script (Stratagene) or pcDNA3 (Invitrogen). The gene of interest includes, but is not limited to a gene within a library of clones, a known gene or a portion thereof, or a mutant of a known gene or a portion thereof. The mammalian expression vector without the gene of interest should be used as a negative control to ensure that the effect observed is not caused by the introduction of viral promoters (e.g., CMV, RSV, or SV40) or other proteins expressed from the plasmid. Depending on the purpose of the experiment, other controls such as a nonactivatable mutant of the fusion trans-activator protein may be included. Methods of generating and using libraries, as well as methods of mutagenesis are well known in the art. See, for example, Ausubel et al. (1988, supra), and Sambrook et al. (1989, supra).

Typical initial experiments for a CHOP km-reporting system are outlined in Tables I and II. As all assays are to be run in triplicate, eight samples will utilize four 6-well tissue culture dishes. Sample numbers are indicated in Column A. Column B indicates volumes of reporter plasmid to use. Column C indicates the amount of fusion trans-activator plasmid to be used in each sample. Column D indicates the amount of pFC2-DBD (negative control for the pFA plasmid to ensure the effects observed are not due to the GALA DNA binding domain; a similar control should be included for other DNA-binding domains) to be used in each sample. Column E indicates the appropriate volume of positive control upstream activator expression plasmid (specific to the pathway being examined) to be used. Column F indicates volumes of the experimental mammalian expression plasmid containing the gene of interest. Column G indicates amounts of the negative control for the plasmid used to express the gene of interest (i.e., plasmid without an inserted gene of interest). Column H indicates the amount of unrelated plasmid DNA containing no mammalian promoters or other elements to be used to keep the amount of DNA in each sample constant.

Table I outlines an approach to evaluating the effect of a gene product on the CHOP pathway that uses transient transfection of all system constituents. The RCLH-CHOP cells of the invention may also be used to evaluate the effect of a gene product on the CHOP pathway, with the advantage that the amount of reporter and fusion transactivator plasmids will be constant in all samples, thereby removing a major source of inaccuracy in this type of assay. In addition, the use of stable CHOP reporter cell lines avoids the potential for promoter interference that exists when multiple different expression/reporter plasmids are transiently transfected into a cell. That is, in the stable system, there should be little or no competition among transfected plasmids for transcription factors necessary for the expression of the transfected genes.

To examine the effect of a gene product on the CHOP activation pathway using RCLH-CHOP cells, one may transfect a vector expressing the gene product or an empty vector into the cells and compare the activity of the reporter in both cases. Performed in the absence of an activating signal this method will assay for activators of the CHOP pathway. Performed in the presence of an activating signal (as described herein), the method will assay for both activators and inhibitors of the CHOP pathway. This approach is well suited for identifying a dominant negative or constitutively active regulatory factor mutant.

A gene of interest may be determined to influence the CHOP pathway if its expression results in a 10% or greater change in the level of reporter expression or activity after consideration of the relevant positive and negative controls.

with stable cell lines described here in combination with dominant negative mutants. In the above Example, GAL4-CHOP fusion protein in the RCLH-CHOP cells was activated by MEK3 expression. A dominant negative form of a gene that acts upstream of MEK3 will not inhibit luciferase expression resulting from the activation of the MAPK pathway in the cell. However, if a gene acts downstream of MEK3, the dominant negative mutant of this gene will be able to inhibit the luciferase expression. By using different genes to activate the pathway leading to CHOP activation, the exact point of action of a gene product can be determined. These types of experiments have previously been performed using transient assays. The ability to make pathway-specific reporter cell lines as described herein greatly facilitates the analysis of signal transduction pathways, including determining the exact point at which an inhibitor or activator of the pathway functions.

Example 3

Assay to Screen for a Modulator of CHOP Signal Transduction Pathways

An assay to screen for a modulator of a specific signal transduction pathway may comprise the following steps:

1) A reporter cell line stably transfected with a construct encoding a transactivator fusion protein responsive to signals in the specific signal transduction pathway being examined is treated with an activator of the signal transduction pathway (e.g., TNF-treatment or p38 MAPK transfection) in the presence and in the absence of a candidate modulator compound. The activator may be a known chemical inducer of the signal transduction

TABLE 1

Sample Experiment to Study the Effects of a Gene Product

| A | B # | C Fusion transactivator plasmid[a] | D pFC2-DBD (negative control for pFA plasmid) | E Positive control | F Experimental plasmid with gene of interest | G Experimental plasmid without insert | H Plasmid DNA |
|---|---|---|---|---|---|---|---|
| 1[b] | 1.0 g(l) | 50 ng(2 l) | — | — | — | 50 ng | 950 ng |
| 2[c] | 1.0 g(l) | 50 ng(2 l) | — | — | — | 100 ng | 900 ng |
| 3[d] | 1.0 g(l) | 50 ng(2 l) | — | — | — | 1000 ng | — |
| 4[e] | 1.0 g(l) | 50 ng(2 l) | — | — | 50 ng | — | 950 ng |
| 5[f] | 1.0 g(l) | 50 ng(2 l) | — | — | 100 ng | — | 900 ng |
| 6[g] | 1.0 g(l) | 50 ng(2 l) | — | — | 1000 ng | — | — |
| 7[h] | 1.0 g(l) | 50 ng(2 l) | — | 50 ng (2 l) | — | — | 950 ng |
| 8[i] | 1.0 g(l) | — | — | 100 ng | — | 850 ng | |

[a]This quantity may need to be optimized, usually within the range of 1–100 ng.
[b]Sample 1 lacks the gene of interest and, therefore, controls for sample 4.
[c]Sample 2 lacks the gene of interest and, therefore, controls for sample 5.
[d]Sample 3 lacks the gene of interest and, therefore, controls for sample 6.
[e]Sample 4 measures the effect of the gene product on the signal transduction pathway involved.
[f]Sample 5 measures the effect of the gene product on the signal transduction pathway involved.
[g]Sample 6 measures the effect of the gene product on the signal transduction pathway involved.
[h]Sample 7 measures the efficacy of the assay for the cell line chosen.
[i]Sample 8 does not contain an activation domain and should show results similar to samples 1–3.

Example 2

Mapping Signal Transduction Pathways Using RCLH-CHOP Stable Reporter Cells

Specific metabolic inhibitors and knockout mutant strains have played an essential role in the mapping of biochemical pathways and signal transduction pathways. The point of action of a gene product along a signal transduction pathway converging at a transcription pathway can be mapped out pathway, a growth factor known to activate the signal transduction pathway, or an agent or treatment that induces expression of an activator of the pathway. This includes expression of a candidate modulator protein from a library of candidate genes cloned into an expression vector that directs high expression in the chosen cell type.

2) Reporter activity is detected in the cells, with a change or difference (of 10% or more) in reporter activity in the presence of the candidate modulator relative to the absence of the candidate modulator being indicative of modulatory activity of the candidate modulator.

Many components of signal transduction pathways are actual or potential targets for drug development. As a means of easy readout for signal transduction pathways, stable reporter cell lines containing fusion transactivators are suitable for high throughput screening. The advantages of using stable cell lines include improved consistency, lower background signal and ease of use.

Example 4

Examining the Effect of an Extracellular Stimulus on CHOP Signal Transduction Pathways The stable CHOP reporter cell line systems described herein may also be used to study the effects of extracellular stimuli, such as growth factors, cellular stresses or drug candidates, on corresponding signal transduction pathways. Table II shows sample conditions for the assay of extracellular stimuli on a specific pathway using transient transfection assays. Cells are transfected with the fusion transactivator plasmid and then treated with the stimulus of interest. The same experiment may be performed without the need for transfection of reporter and fusion transactivator using the stable RCLH-CHOP cell lines of the invention. Reporter expression from the reporter plasmid indicates the activation of the fusion transactivator protein and, therefore, the presence and/or activity of the endogenous protein kinase specific to the activation pathway. Changes or differences in the expression of reporter in response to extracellular stimuli are therefore indicative of effects of those extracellular stimuli on the CHOP pathway.

TABLE II

Sample Experiment to Study the Effects of Extracellular Stimuli

| # | pFR-Luc Plasmid (reporter plasmid) | Fusion trans-activator Plasmid[a] | pFC2-DBD (negative control) | Positive control | Extracellular stimuli |
|---|---|---|---|---|---|
| 1[b] | 1.0 g(l) | — | 50 ng(2 l) | — | Serum(10%) |
| 2[c] | 1.0 g(l) | 50 ng(2 l) | — | — | Serum(10%) |
| 3[d] | 1.0 g(l) | — | 50 ng(2 l) | — | EGF(100 ng/ml) |
| 4[e] | 1.0 g(l) | 50 ng(2 l) | — | — | EGF(100 ng/ml) |
| 5[f] | 1.0 g(l) | — | 50 ng(2 l) | — | Medium |
| 6[g] | 1.0 g(l) | 50 ng(2 l) | — | — | Medium |
| 7[h] | 1.0 g(l) | 50 ng(2 l) | — | 50 ng(2 l) | — |
| 8[i] | 1.0 g(l) | — | 50 ng(2 l) | — | — |

[a]This quantity may need to be optimized, usually within the range of 1–100 ng.
[b]Sample 1 lacks the fusion trans-activator protein and, therefore, controls for sample.
[c]Sample 2 measures the effect of fetal bovine serum on kinase activation.
[d]Sample 3 lacks the fusion trans-activator protein and, therefore, controls for sample 4.
[e]Sample 4 measures the effect of EGF on kinase activation.
[f]Sample 5 controls for the extracellular stimulus as well as the fusion trans-activator protein.

Other Embodiments

Other embodiments will be evident to those of skill in the art. It should be understood that the foregoing detailed description is provided for clarity only and is merely exemplary.

The spirit and scope of the present invention are not limited to the above examples, but are encompassed by the following claims.

What is claimed is:

1. A cell line comprising a stably integrated recombinant nucleic acid construct comprising: a reporter gene operably linked to a recognition sequence for a sequence-specific DNA-binding protein: and a stably integrated recombinant nucleic acid construct comprising a sequence encoding a fusion protein, said fusion protein comprising a sequence-specific DNA binding domain, wherein said DNA binding domain specifically binds said recognition sequence, and a conditionally active transactivation domain of CHOP, wherein bindings of said fusion protein to said recognition sequence results in transactivation of said reporter gene when said transactivation domain fused to said DNA binding domain is activated, and wherein said sequence-specific DNA binding domain of said fusion protein is located upstream of said conditionally active transactivation domain of CHOP, wherein said recognition sequence for a sequence-specific DNA-binding domain is that sequence recognized by one of the group consisting of GAL4 and LexA.

* * * * *